United States Patent
Deng et al.

(10) Patent No.: US 12,018,278 B2
(45) Date of Patent: Jun. 25, 2024

(54) METHODS FOR CHEMICALLY INDUCED LINEAGE REPROGRAMMING

(71) Applicants: BeiHao Stem Cell and Regenerative Medicine Research Institute Co., Ltd., Guangdong (CN); HONG GUAN LTD., Beijing (CN)

(72) Inventors: Hongkui Deng, Beijing (CN); Xiang Li, Beijing (CN); Defang Liu, Beijing (CN); Yantao Ma, Beijing (CN); Xiaomin Du, Beijing (CN)

(73) Assignees: BeiHao Stem Cell and Regenerative Medicine Research Institute Co., Ltd., Guangdong (CN); HONG GUAN LTD., Beijing (CN)

( * ) Notice: Subject to any disclaimer, the term of this patent is extended or adjusted under 35 U.S.C. 154(b) by 612 days.

(21) Appl. No.: 16/618,531

(22) PCT Filed: May 31, 2017

(86) PCT No.: PCT/CN2017/086545
§ 371 (c)(1),
(2) Date: Dec. 2, 2019

(87) PCT Pub. No.: WO2018/218480
PCT Pub. Date: Dec. 6, 2018

(65) Prior Publication Data
US 2020/0277567 A1    Sep. 3, 2020

(51) Int. Cl.
*C12N 5/073* (2010.01)

(52) U.S. Cl.
CPC ........ *C12N 5/0603* (2013.01); *C12N 2501/01* (2013.01); *C12N 2501/065* (2013.01); *C12N 2501/15* (2013.01); *C12N 2501/385* (2013.01); *C12N 2501/999* (2013.01)

(58) Field of Classification Search
CPC .............. C12N 5/0603; C12N 2501/01; C12N 2501/065; C12N 2501/15; C12N 2501/385; C12N 2501/999
See application file for complete search history.

(56) References Cited

U.S. PATENT DOCUMENTS

| | | |
|---|---|---|
| 5,716,404 A | 2/1998 | Vacanti |
| 6,962,814 B2 | 11/2005 | Mitchell |
| 7,914,579 B2 | 3/2011 | Vacanti |
| 8,728,495 B2 | 5/2014 | Sevrain |
| 2006/0019326 A1 | 1/2006 | Vacanti |
| 2007/0059293 A1 | 3/2007 | Atala |
| 2008/0206733 A1 | 8/2008 | Tanaka |
| 2009/0029322 A1 | 1/2009 | Duailibi |
| 2016/0068816 A1 | 3/2016 | Osafune |

FOREIGN PATENT DOCUMENTS

| | | | | |
|---|---|---|---|---|
| CN | 102260646 | | 11/2011 | |
| CN | 102741394 | | 10/2012 | |
| CN | 104278008 | | 1/2015 | |
| CN | 105039258 | | 11/2015 | |
| CN | 105441384 A | * | 3/2016 | .......... C12N 5/0735 |
| CN | 108934168 | | 12/2018 | |
| CN | 110799641 | | 2/2020 | |
| WO | WO2015003643 A1 | * | 1/2015 | ............. C12N 5/071 |
| WO | 2017091943 | | 6/2017 | |

OTHER PUBLICATIONS

Wang et al., Rapid and efficient reprogramming of somatic cells to induce pluripotent stem cells by retinoic acid receptor gamma and liver receptor homolog 1, PNAS, 108(45): 18283-18288. (Year: 2011).*
Storm et al., Regulation of Nanog Expression by Phosphoinositide 3-Kinase-dependent Signaling in Murine Embryonic Stem Cells, Journal of Biological Chemistry, 282(9): 6265-6273. (Year: 2007).*
Silva et al., Nanog Is the Gateway to the Pluripotent Ground State, Cell, 138: 722-737. (Year: 2009).*
Deng et al., Compositions and Methods for Reprograming Non-Pluripotent Cells Into Pluripotent Stem Cells, machine translation of CN 104278008 A. (Year: 2015).*
McClean et al., The emerging roles of DOT1L in leukemia and normal development, Leukemia, 28:2131-2138. (Year: 2014).*
Webster's Dictionary, "kit" definition, retrieved from internet Aug. 8, 2022. (Year: 2011).*
Deng et al., CN105441384 A, Machine translation. (Year: 2016).*
Ambasudhan, et al., "Direct Reprogramming of Adult Human fibroblasts to Functional Neurons under Defined Conditions", *Cell Stem Cell*, 9(2): 113-118 (2001).
Balladur, et al., "Transplantation of allogeneic hepatocytes without immunosuppression: Long-term survival", *Surger*, 117: 189-94 (1995).
Banerjee, et al., "Human Embryonic Stem Cells Differentiated to Lung Lineage-Specific Cells ameliorate Pulmonary fibrosis in a Xenograft Transplant Mouse Model", *PLOS One*, 7(3)e33165 (2012).
Bar-Nur, et al., "Lineage conversion induced by pluripotency factors involves transient passage through an iPS cell stage", *Nat Biotechnol.*, 33:761-768 (2015).

(Continued)

*Primary Examiner* — Laura Schuberg
*Assistant Examiner* — Joseph Paul Miano
(74) *Attorney, Agent, or Firm* — PABST PATENT GROUP LLP

(57) ABSTRACT

Provided are chemical inducers of lineage reprogramming (CiLR) which include glycogen synthase kinase inhibitors, TGFβ receptor inhibitors, cyclic AMP agonists or histone acetylators. Also provided is a method of inducing lineage reprograming in a partially or completely differentiated cell of a first type into a cell with characteristics of a second and different lineage. The method includes: contacting a cell with the CiLR for a sufficient period of time to result in reprograming the cell into a modified XEN-like cell which is subsequently programmed into a cell with characteristics of a second and different lineage.

6 Claims, 16 Drawing Sheets
Specification includes a Sequence Listing.

(56) References Cited

OTHER PUBLICATIONS

Cai, et al., "Directed differentiation of human embyonic stem cells into functional hepatic cells", *Hepatology*, 45: 1229-1239 (2007).
Dixit, et al., "Repeated Cell Transplantation of Microencapsulated Hepatocytes for Sustained Correction of Hyperbilirubinemia in Gunn Rats", *Cell Transplantation*, 1:275-79 (1992).
Ho, et al., "NeurophologyJ: An automatic neuronal morphology quantification method and its application in pharmacological discovery", *BMC Bioinformatics*, 12(230):1-18 (2011).
Hu, et al., "Direct Conversion of Normal and Alzheimer's Disease Human Fibroblasts into Neuronal Cells by Small Molecules", *Cell Stem Cell*, 17:204-212 (2015).
Izant, et al., "Microtubule-associated Proteins: A Monoclonal Antibody to MAP2 Binds to Differentiated Neurons", *Proc. Natl. Acad. Sci. USA.*, 77:4741-5 (1980).
Kanaani, et al., "Two Distinct Mechanisms Target GAD67 to Vesicular Pathways and Presynaptic Clusters", *J. Cell. Biol.*, 190(5):911-925 (2010).
Kuo, et al., "Synthesis and Discovery of macrocyclic Polyoxygenated bis-7-azaindolylmaleimides as a Novel Series of potent and Highly Selective Glycogen Synthase kinase-3beta Inhibitors", *J. Med Chem.*, 6:4021-4031 (2003).
Lee, et al., "Histone H3 Lysine 4 Demethylation Is a Target of Nonselective antidepressive Medications", *Chem. and Biol.*, 13:563-567 (2006).
Li, et al., "Small-Molecule-Driven Direct Reprogramming of Mouse Fibroblasts into Functional Neurons", *Cell Stem Cell*, 17:195-203 (2015).
Liu, et al., "Systematically labeling developmental stage-specific genes for the study of pancreatic beta-cell differentiation from human embryonic stem cells", *Cell Res.*, 24(10): 1181-1200 (2014).
Mhanna, et al., "GFOGER-modified MMP-sensitive Polyethylene Glycol Hydrogels Induce Chondrogenic Differentiation of Human Mesenchymal Stem Cells", *Tissue engineering Part A.*, 20(7-8): 1165-74 (2014).
Mullen, et al., "NeuN, a neuronal specific nuclear protein in vertebrates", *Development*, 116:201-11 (1992).
Parekh, et al., "Neuronal Morphology Goes Digital: A Research Hub for Cellular and System Neuroscience", *Neuron*, 77(6): 1017-1038 (2013).
Patima, "Neuronal Cell Markers", *Mater. Methods*, 3:196 (2013).
Schmitt, et al., "Nonpeptidic Propargylamines as Inhibitors of Lysine Specific demethylase 1 (LSD1) with Cellular Activity", *J. Med Chem.*, 56 (18): 7334-7342 (2013).
Shapiro, et al., "Islet Transplantation in Seven Patients with Type 1 diabetes mellitus Using a Glucocorticoid-Free Immunosuppressive Regimen", *N. Engl. J. Med.*, 343(4):230-8 (2000).
Song, et al., "Efficient generation of hepatocyte-like cells from human induced pluripotent stem cells", *Cell Res.*, 19: 1233-1242 (2009).
Vierbuchen, et al.. , "Direct conversion of fibroblasts to functional neurons by defined factors", *Nature*, 463:1035-1041 (2010).
Willerth, et al., "Combining stem cells and biomaterial scaffolds for constructing tissues and cell delivery", *Journal of StemJournal*, 1(2019): 1-25 (2008).
Wojcik, et al., "An essential role for vesicular glutamate transporter 1 (VGLUT1) in postnatal development and control of quantal size", *PNAS*, 101(18):7158-7163 (2004).
Xin, et al., "Insulin-Producing Cells Differentiated from Human Bone Marrow Mesenchymal Stem Cells In Vitro Ameliorate Sterptozotocin-Induced Diabetic Hyperglycemia", *PLOS One*, 11(1):0145838 (2016).
Xu, et al., "Direct Lineage Reprogramming: Strategies, Mechanisms, and Applications", *Cell Stem Cell*, 16:119-134 (2015).
Yang, et al., "High efficient isolation and systematic identification of human adipose-derived mesenchymal stem cells", *J. Biomed. Sci.*, 18(59):1-9 (2011).
Yoo, et al., "MicroRNA-mediated conversion of human fibroblasts to neurons", *Nature*, 476(7359):228-31 (2011).
Zhang, et al., "Quantification of Retinogenesis in 3D Cultures Reveals Epigenetic Memory and Higher Efficiency in iPSCs Derived from Rod Photoreceptors", *Cell Stem Cell*, 17: 101-115 (2015).
Zhao, et al., "A XEN-Like State Bridges Somatic Cells to Pluripotency During Chemical Reprogramming", *Cell*, 163:1678-1691 (2015).
Zhou, et al., "Decellularized Liver Matrix as a Carrier for the Transplantation of Human Fetal and Primary Hepatocytes in Mice", *Liver Transpl . . .* , 17(4):418-27 (2011).
Zhou, et al., "Identification of Novel Selective Lysine-specific Demethylase 1 (LSD1) Inhibitors Using a Pharmacophore-Based Virtual Screening Combined With Docking", *Chem. Biol. and Drug Design*, 85(6):659-671 (2015).
International Search Report for PCT/CN2017/086545 dated Feb. 8, 2018.
De Los Angeles, et al., "A chemical logic for reporgramming to pluripotency", Cell Research, 23(12):1337-1338 (2013).
Lu, et al., "Small molecules and small molecule drugs in regenerative medicine", Drug Discovery Today, 19(6): 801-808 (2014).
Extended European search Report for European Application No. 17911423.6 dated Nov. 26, 2020.
Balladur, et al., "Transplantation of allogeneic hepatocytes without immunosuppression: Long-term survival", Surgery, 117: 189-94 (1995).
Li, et al., "Direct Reprogramming of Fibroblasts via a Chemically Induce XEN-like State", Cell Stem Cell, 21:1-10 (2017).
Office Action CN (China) Application No. 201780090055.8 dated Dec. 5, 2022.
Zhang, et al., "Cell direct reprogramming technology-new strategies for the treatment of disease", Chines Bulletin of Life Sciences, 26(4): 400-406 (2014). with English Abstract.

* cited by examiner

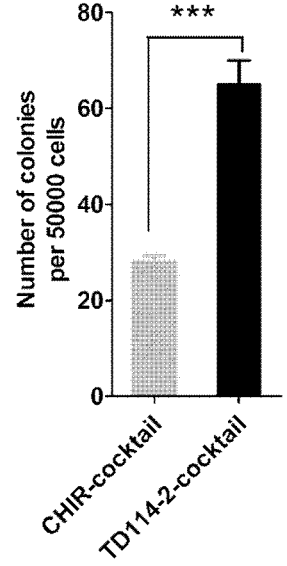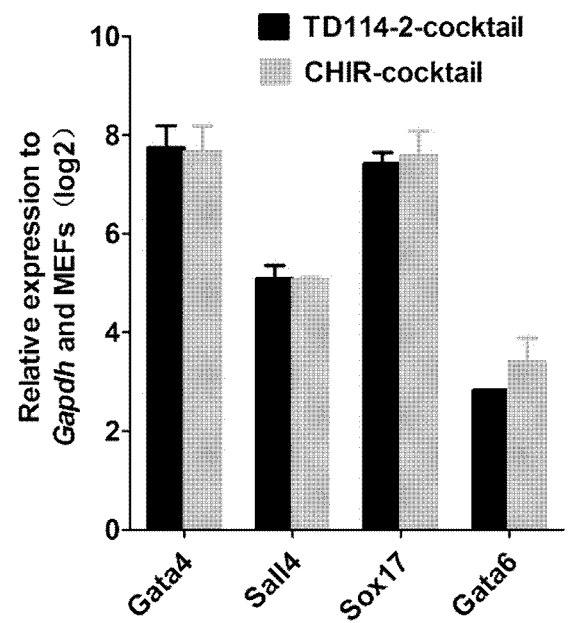
FIG. 1A
FIG. 1B
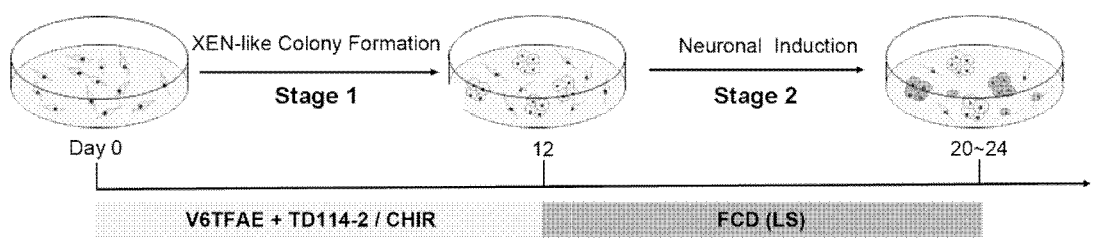
FIG. 1C

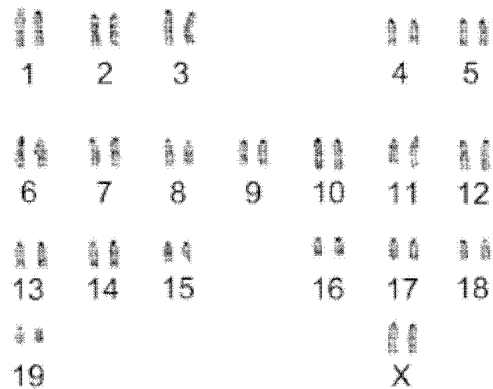
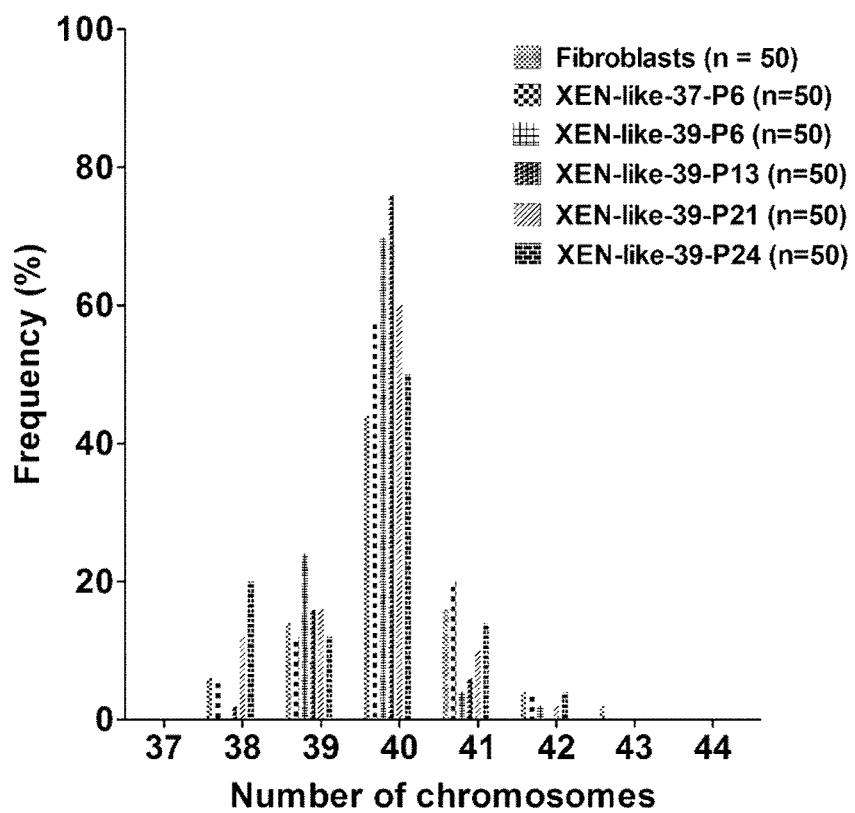
FIG. 4B
FIG. 4C 006545, filed May 31, 2017, the disclosure of which is
METHODS FOR CHEMICALLY INDUCED LINEAGE REPROGRAMMING

CROSS-REFERENCE TO RELATED APPLICATIONS

This application is a 371 application of PCT/CN2017/086545, filed May 31, 2017, the disclosure of which is hereby incorporated herein by reference in its entirety.

REFERENCE TO SEQUENCE LISTING

The Sequence Listing submitted Apr. 20, 2020 as a text file named "HGL_103_ST25.txt," created on Apr. 20, 2020, and having a size of 10,672 bytes is hereby incorporated by reference.

FIELD OF THE INVENTION

The present invention generally relates to small molecule compositions and methods for chemically transdifferentiating cells.

BACKGROUND OF THE INVENTION

Direct lineage reprogramming has emerged as a promising strategy to induce cell fate direct transition by introducing a combination of cell-type-specific transcription factors and has made remarkable advances in generating diverse cell types bypassing the tumorigenic pluripotent stage. Chemical reprogramming has emerged as a new approach to generate different functional cell types. Compared with the transgenic approaches to induce lineage reprogramming, chemical approaches have advantages, because they use small-molecule compounds that are cell-permeable, reversible and easily manufactured, and can be fine-tuned in terms of concentration, duration, structure, and combination. The feasibility of generating chemically induced neurons (CiNs) from mouse and human cells has been demonstrated (Li et al., Cell Stem Cell, 17:195-203 (2015); Hu et al., Cell Stem Cell, 17:204-212 (2015); Zhang et al., Cell Stem Cell, 17:1-13 (2015)). These findings provide an alternative methodology for studying cell fate plasticity and generating functional desirable cell types, thus avoiding the risk of genome integration through use of exogenous transcriptional factors. However, limited cell yield in direct reprogramming strategy is a major drawback for future applications. It is desirable to provide methods to improve reprogramming kinetics and functional maturity of the induced cells It is an object of the present invention to provide a combination of small molecules which can be used for lineage reprograming of cells.

It is also an object of the present invention to provide a method of reprograming cells from one lineage to a second lineage.

It is a further object of the present invention to provide chemically reprogramed cells.

SUMMARY OF THE INVENTION

Compositions and methods are disclosed for improving the efficiency of chemically reprograming cells of a first lineage or type, to cells of a second (and different) lineage or type. The methods are based on the discovery of the plasticity of XEN-like state which allows for chemical treatment to bypass pluripotency and convert a cell of a first type/lineage, chemically induced into a modified XEN-like state, into a cell of a second type/lineage.

Accordingly, small molecule cocktails, herein, chemical inducers of lineage reprograming (CiLR), have been identified which can be used to enhance reprogramming of partially or completely differentiated cells into modified a XEN-like state. Cells in the modified Xen-like state can subsequently be reprogrammed into cells of a different/second lineage. The CiLR include (1) a glycogen synthase kinase (GSK) inhibitor, (2) a TGFβ receptor inhibitor, (3) a cyclic AMP agonist, (4) a histone acetylator/deacetylase inhibitor (5) a DOT1L methyltransferase inhibitor, (6) a retinoic acid receptor (RAR) agonist, and (7) an inhibitor of histone demethylation and combinations thereof.

In one embodiment, the GSK inhibitors is the aminopyrimidine, CHIR99021 ("C") [6-[[2-[[4-(2,4-Dichlorophenyl)-5-(5-methyl-1H-imidazol-2-yl)-2-pyrimidinyl]amino]ethyl]amino]-3-pyridinecarbonitrile]. In a preferred embodiment the GSK inhibitor is TD114-2, having the chemical name ((10,11,13,14,16,17,19,20,22,23-decahydro-9,4:24, 29-dimetheno-1H-dibenzo[n,t] pyrrolo[3,4-q] [1,4,7,10,13,22]-tetraoxadiazacyclotetracosine-31,33(32H) dione)) ("TD114-2"); preferred TGFβ receptor inhibitors include 616452 ("6"); SB431542 (4-[4-(1,3-benzodioxol-5-yl)-5-(2-pyridinyl)-1H-imidazol-2-yl]benzamide) ("S"); LDN193189 (4-(6-(4-(piperazin-1-yl)phenyl)pyrazolo[1,5-a]pyrimidin-3-yl)quinolone) ("L") and dosomorphine ("D"); the cAMP agonist is Forskolin (FSK;"F"). A preferred methyltransferase inhibitor is EPZ004777, "1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea ("E"). A preferred RAR agonists include AM 580 ("A") (4-[(5,6,7,8-Tetrahydro-5,5,8,8-tetramethyl-2-naphthalenyl)carboxamido]benzoic acid). A preferred inhibitor of histone demethylation is tranylcypromine ("T"). A preferred a histone acetylator/deacetylase inhibitor is as valproic acid ("V").

Also provided is a method of enhancing lineage reprograming of a cell of a first type, to a cell of a second type/lineage. Preferred cells to reprogram include fibroblast cells, adipose-derived stem cells (ADSC), neural derived stem cells and intestinal epithelial cells. In a preferred embodiment, the method also does not include contacting the cell to be reprogrammed with a polypeptide such as a transcription factor. The method disclosed herein includes the steps of (a) contacting the cell to be reprogrammed with a first cocktail of CiLR (herein, modified XEN-Cocktail) for a sufficient period of time to bias the cells into a modified XEN-like cell population; and (b) culturing the population of modified XEN-like cells for a sufficient period of time to reprogram the cell into a cell of a second cell type/lineage (CiLRC) in lineage specific induction/differentiation cell culture media which included compounds that bias the Xen-like cells towards the specific lineage (herein, Lineage specific media).

Isolated chemically induced lineage reprogrammed cells (CiLRCs), are not naturally occurring cells. CiLRCs possess a hybrid of properties belonging to cells of the second lineage to which they are reprogrammed such as morphology, similar doubling time, expression of the second lineage-specific markers; however, the cells retaining characteristics from the first cell type from which they are obtained. For example if the cell of the first type is a fibroblast, reprogrammed into a neuron-like cell, the CiLRCs are neuron-like, morphologically and functionally.

In a preferred embodiment, the CiLRCs are not genetically engineered, i.e., the CiLRCs are not obtained by a method which includes introducing or removing genetic elements from the cells. However, CiLRCs disclosed herein can be distinguished from the cells in the lineage to which they are reprogrammed at least by the methods that are used to generate them i.e., by their origin. Whereas the cell of the first type are naturally occurring cells, CiLRCs on the other hand are not naturally occurring and are obtained by culturing cells of a first linage with a combination of small molecules, as described herein.

The CiLRCs can be used in a number of applications, including but not limited to cell therapy and tissue engineering.

BRIEF DESCRIPTION OF THE DRAWINGS

FIG. 1A shows RT-qPCR analysis of XEN master genes (GATA4, SALL4, SOX17 and GATA6) by chemical induction with TD114-2-cocktail or CHIR-cocktail). n=2; FIG. 1B is a bar graph showing co-immunostainings (Gata4, Sall4, Sox17 and Gata6) for the primary colonies induced by TD114-2-cocktail. FIG. 1C is a schematic diagram of the XEN-like state based chemical reprogramming approach.

FIG. 4B shows karyotype analysis of chemically induced XEN-like cells; FIG. 4C shows distribution of chromosome numbers in passaged XEN-like cells. n indicates the number of cells analyzed. Comparative genomic hybridization (CGH) analysis of chemically induced)(EN-like cells. Average log 2 ratio values are plotted using fibroblasts as a reference.

DETAILED DESCRIPTION OF THE INVENTION

I. Definitions

Figure 1D:
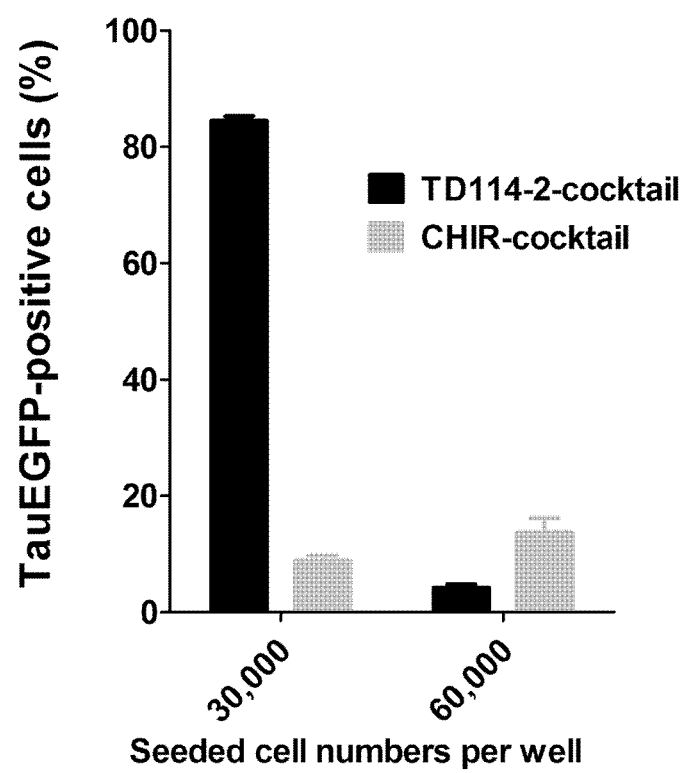
FIG. 1D is a bar graph showing efficiency of TauEGFP-positive cells induced by TD114-2-cocktail or CHIR-cocktail with different starting cell density (determined by FACS). n=2. The data are presented as the mean+/−SEM. *P<0.05; P<0.01; *P<0.001 (Student's t-test)

The term "chemically induced lineage reprogrammed cells" (CiLRCs) as used herein refers to cells with characteristic of at least one cell lineage, that derived from a cell of a first type that is different in type/lineage, by contacting the cell of a first type/lineage with chemical compounds, not by expression of one or more transfected genes.

As used herein a "culture" means a population of cells grown in a medium and optionally passaged. A cell culture may be a primary culture (e.g., a culture that has not been passaged) or may be a secondary or subsequent culture (e.g., a population of cells which have been subcultured or passaged one or more times).

As used herein "enhancing", or "increasing" the efficiency of reprogramming means reducing to total reprograming time and/or increasing the number of reprogrammed cells obtained from the same starting cell density the same length of time when compared to a chemical reprograming method that does not proceed via biasing the cells to be programing towards a XEN-like state.

The term "Induced pluripotent stem cell" (iPSC), as used herein, is a type of pluripotent stem cell artificially derived from a non-pluripotent cell.

The term "isolated" or "purified" when referring to CiLRCs means chemically induced reprogrammed cells at least 30%, 35%, 40%, 45%, 50%, 55%, 60%, 65%, 70%, 75%, 80%, 85%, 90%, 95%, or 99% free of contaminating cell types such as non-lineage reprogrammed cells. The isolated stem cells may also be substantially free of soluble, naturally occurring molecules.

"Neuron-like" when used to refer to a reprogrammed cell refers to the cell possessing properties normally attributed to neurons/nerve cells i.e., "neuron-like properties" such as morphology (for example neurite outgrowth), expression of neuronal-specific markers such as MAP2, NF-H, mature neuronal markers such as NeuN, excitatory or inhibitory membrane properties as evidenced by expression of vGlut and/or Gad67, and membrane depolarization as measured in a patch-clamp assay.

"Neuronal-like morphology" is used herein interchangeably with "neuron-morphology" to refer to morphology characteristic of neurons, such as the presence of a soma/cell body, dendrites, axon and/or synapses.

"Non-neuronal cells" as used herein refers to cells which are not characterized as neurons based on a combination of morphology and functions associated with neurons.

The term "pluripotency" (or pluripotent), as used herein refers to a stem cell that has the potential to differentiate into any of the three germ layers: endoderm (for example, interior stomach lining, gastrointestinal tract, the lungs), mesoderm (for example, muscle, bone, blood, urogenital), or ectoderm (for example, epidermal tissues and nervous system). The term "not pluripotent" means that the cell does not have the potential to differentiate into all of the three germ layers. A multipotent stem cell is less plastic and more differentiated, and can become one of several types of cells within a given organ. For example, multipotent blood stem cells can develop into red blood cell progenitors, white blood cells or platelet producing cells. Adult stem cells are multipotent stem cells. Adipose-derived stem cells are multipotent.

"Reprogramming" as used herein refers to the conversion of a one specific cell type to another and it includes inducing one differentiated cell type to express markers known for a different differentiated cell type which can be of ectodermal, mesodermal or endodermal origin. For example, a non-neuronal cell such as a fibroblast can be reprogrammed into cell with neuron-like properties. Where the cell of the first type is reprogrammed into a cell of a second and different type/linage using chemical compounds, the resulting cell is a chemically induced lineage reprogrammed (CiLR) neuron.

The term "small molecule" refers to a molecule, such as an organic or organometallic compound, with a molecular weight of less than 2,000 Daltons, more preferably less than 1,500 Daltons, most preferably less than 1,000 Daltons.

"XEN-like cells" are used herein refers to cells which are characterized as epithelial cells, and which express XEN markers such as SALL4, GATA4, GATA6 and SOX17. XEN-like state when used connection with cells refers to expression of one or more XEN markers.

II. Compositions

A. Small Molecules Inducing Lineage Reprograming

Chemical compounds that induce lineage reprogramming i.e., chemical inducers of lineage reprograming (CiLR) include small molecules having a molecular weight of less than 2,000 Daltons, more preferably less than 1,500 Daltons, most preferably less than 1,000 Dalton, alone or in combination with proteins. The small molecules may have a molecular weight less than or equal to 900 Daltons or, less than or equal to 500 Daltons. Larger molecules can be used in chemically-induced reprogramming, preferably targeting the same pathway as the small molecules identified here. Several protein factors, such as recombinant bFGF, have been demonstrated to be effective in the following protocol for chemical reprogramming.

Accordingly, small molecule cocktails have been identified which can be used to enhance reprogramming of partially or completely differentiated cells of a first type/lineage into a modified XEN-like state and subsequently, into cells of a second and different type/lineage The CiLRs include (1) a glycogen synthase kinase (GSK) inhibitor, (2) a TGFβ receptor inhibitor, (3) a cyclic AMP agonist, (4) a histone acetylator/deacetylase inhibitor (5) a DOT1L methyltransferase inhibitor, (6) a retinoic acid receptor (RAR) agonist, and (7) an inhibitor of histone demethylation and combinations thereof.

(1). GSK Inhibitors

Preferred GSK inhibitors include the aminopyrimidine, CHIR99021 ("C"), preferably used in a concentration of from 1 to 30 µM, more preferably, between 10-20 µM and TD114-2 ("T") having the structure shown below, preferably used in a concentration from 0.2 to 20 µM, more preferably, from 2-6 µM, most preferably, from 2-4 µM.

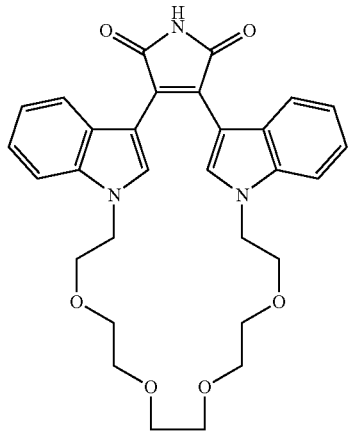

TD114-2

In some preferred embodiments, the small molecule cocktail does not include CHIR99021.

Other GSK inhibitors can also be used in the methods disclosed herein, and they include, but are not limited to BIO-acetoxime (for example 1 µM); GSK 31 inhibitor XV; SB-216763; CHIR 99021 trihydrochloride, which is the hydrochloride salt of CHIR99021; GSK-3 Inhibitor IX [((2Z,3E)-6'-bromo-3-(hydroxyimino)[2,3'-biindolinylidene]-2'-one]; GSK 3 IX [6-Bromoindirubin-3'-oxime]; GSK-3β Inhibitor XII [3-[[6-(3-Aminophenyl)-7H-pyrrolo [2,3-d]pyrimidin-4-yl]oxy]phenol]; GSK-3 Inhibitor XVI [6-(2-(4-(2,4-dichlorophenyl)-5-(4-methyl-1H-imidazol-2-yl)-pyrimidin-2-ylamino)ethyl-amino)-nicotinonitrile]; SB-415286 [3-[(3-chloro-4-hydroxyphenyl)amino]-4-(2-nitrophenyl)-1H-pyrrole-2,5-dione]; and Bio [(2'Z,3'E)-6-bromoindirubin-3'-oxime], used at a concentration equivalent to 20 µM CHIR99021.

(2). TGFβ Receptor Inhibitors

The TGFβ inhibitor is preferably inhibits the TGFβ type 1 receptor activating receptor-like kinase (ALK) 5, ALK 2, ALK 3 and ALK 4, alone or in combination, and the nodal type receptor 1 receptor ALK7 in other embodiments Preferred TGFβ receptor inhibitors include 616452 ("6"), preferably used in a concentration ranging from 1-30 µM, preferably, between 5 and 10 µM, for example, 6, 7 8, 9 or 10 µM; SB431542 ("S"), preferably used in a concentration range from 0.2 to 20 µM, more preferably, from 2-10 µM, and even more preferably from 2-5 µM; LDN 193189 ("L"), preferably used in a concentration between 0.01 and 10 µM, more preferably, between 0.01 and 1 even more preferably, from 0.1-1 µM and dosomorphine ("D"), preferably used at a concentration between 0.1-10 µM, preferably between 1-5 µM and more preferably, between 1-2 µM.

Other TGFβ inhibitors are known in the art and are commercially available. Examples include E-616452 [2-(3-(6-Methylpyridin-2-yl)-1H-pyrazol-4-yl)-1,5-naphthyridine]; A 83-01 [3-(6-Methyl-2-pyridinyl)-N-phenyl-4-(4-quinolinyl)-1H-pyrazole-1-carbothioamide]; SB 505124 [2-[4-(1,3-Benzodioxol-5-yl)-2-(1,1-dimethylethyl)-1H-imidazol-5-yl]-6-methyl-pyridine]; GW 788388 [4-[4-[3-(2-Pyridinyl)-1H-pyrazol-4-yl]-2-pyridinyl]-N-(tetrahydro-2H-pyran-4-yl)-benzamide]; and SB 525334 [6-[2-(1,1-Dimethylethyl)-5-(6-methyl-2-pyridinyl)-1H-imidazol-4-yl]quinoxaline].

(3) cAMP Agonists

The preferred cAMP agonist is Forskolin (F), preferably in a concentration range from 5-500 µM, more preferably, from 50-100 µM and even more preferably, between 10-50 µM. Additional cAMP agonist that can be included in the cocktails disclosed herein. Examples include, but are not limited to prostaglandin E2 (PGE2), rolipram, genistein and cAMP analogs such as DBcAMP or 8-bromo-cAMP.

(4). Histone Acetylator/Deacetylase Inhibitors

The preferred histone acetylator is valproic acid ("V"), preferably used in a concentration range from 50-1000 µM, more preferably, between 100 and 500 µM. Other histone deacetylase inhibitors are commercially available and can be used in the disclosed methods. Non-limiting examples include apicidin, CI 994 (N-acetyldinaline 4-(Acetylamino)-N-(2-aminophenyl)benzamide), Depsipeptide, KD 5170 (S-[2-[6-[[[4-[3-(Dimethylamino)propoxy]phenyl]sulfonyl] amino]-3-pyridinyl]-2-oxoethyl]ethanethioc acid ester), sodium, 4-phenyl butyrate, sodium butyrate, UF 010, etc.

(5). DOT1L Methyltransferase Inhibitors

DOT1L methyltransferase inhibitors are preferred. Examples include methyltransferase inhibitors include SGC 0946 (1-[3-[[[(2R,3S,4R,5R)-5-(4-Amino-5-bromo-7H-pyrrolo[2,3-d]pyrimidin-7-yl)-3,4-dihydroxytetrahydrofuran-2-yl]methyl](isopropyl)amino]propyl]-3-[4-(2,2-dimethylethyl)phenyl]urea) and EPZ004777 ("E"). A preferred DOT1L methyltransferase inhibitor is EPZ004777, preferably used in a concentration range from 0.5-20 µM, more preferably, between 1-10 µM and more preferably, between 1-5 µM.

(6). Retinoic Acid Receptor (RAR) Agonists

Examples of RAR agonists include Ch 55 ([4-(1E)-3[3,5-bis(1,1-Dimethylethyl)phenyl]-3-oxo-1-propenyl]benzoic acid], is a highly potent synthetic retinoid that has high affinity for RAR-α and RAR-β receptors and low affinity for cellular retinoic acid binding protein (CRABP)]; AM580 ([4-[(5,6,7,8-Tetrahydro-5,5,8,8-tetramethyl-2-naphthalenyl)carboxamido]benzoic acid]; an analog of retinoic acid that acts as a selective RARα agonist); [4-[(E)-2-(5,6,7,8-Tetrahydro-5,5,8,8-tetramethyl-2-naphthalenyl)-1-propenyl]benzoic acid] (TTNPB).

A preferred RAR agonist is AM 580 ("A"), preferably used in a concentration range from 0.005-1 µM, more preferably from 0.05 to 0.1 µM.

(7). Inhibitors of Histone Demethylation

A preferred inhibitor of histone demethylation is tranylcypromine ("T") preferably used in a concentration range from 0.5-50 µM, more preferably, from 5-20 µM and even more preferably, from 7-15 µM. Tranylcypromine is a non-selective and irreversible monoamine oxidase inhibitor (MAOI). Another useful MAOI which are also inhibitors of histone demethylation include phenelzine (Lee, et al. *Chem and Biol.*, 13:563-567 (2006), Additional non-limiting examples include compound XZ09 disclosed in Zhou, et al., *Chem Biol. and Drug Design,* 85(6):659-671 (2015) and nonpeptide propargylamines (Schmidtt, et al. *J. Med. Chem.*, 56 (18): 7334-7342 (2013).

(8). Additional Small Molecule Boosters

Additional and optional small molecules that can be used to boost reprogramming efficiency include D4476 (D4476 (CAS 301836-43-1) (4-[4-(2,3-Dihydro-1,4-benzodioxin-6-yl)-5-(2-pyridinyl)-1H-imidazol-2-yl]benzamide), a high purity Casein kinase inhibitor and TGF-β type-I receptor (ALK5) inhibitor); ISX9 [N-cyclopropyl-5-(2-thienyl)-3-isoxazolecarboxamide]; bromodomain inhibitors for example I-BET151 having the chemical name [(7-(3,5-dimethylisoxazol-4-yl)-8-methoxy-1-((R)-1-(pyridin-2-yl) ethyl)-1H-imidazo[4,5-c]quinolin-2(3H)-one]; JQ1 having the chemical name [(6S)-4-(4-chlorophenyl)-2,3,9-trimethyl-6H-thieno[3,2-f][1,2,4]triazolo[4,3-a][1,4]diazepine-6-acetic acid 1,1-dimethylethyl ester]; bromosporine; and I-CBP112 having the chemical name [1-[7-(3,4-dimethoxyphenyl)-9-[[(3S)-1-methylpiperidin-3-yl]methoxy]-2,3,4,5-tetrahydro-1,4-benzoxazepin-4-yl]propan-1-one].

A preferred cocktail includes only small molecules from group (1)-(7) above, i.e., the cocktail does not include any of ISX9, I-BET151, JQ1, bromosporine or I-CBP112.

B. Cells to be Induced

The reprogrammed cells are obtained by inducing partially or completely differentiated cells obtained from a mammal such as any mammal (e.g., bovine, ovine, porcine, canine, feline, equine, primate), preferably a human. Sources include bone marrow, fibroblasts, fetal tissue (e.g., fetal liver tissue), peripheral blood, umbilical cord blood, pancreas, skin or any organ or tissue. Useful cell types that can be induced include, but are not limited to: multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells.

The cell to be reprogrammed can be obtained from a sample obtained from a mammalian subject. The subject can be any mammal (e.g., bovine, ovine, porcine, canine, feline, equine, primate), including a human. The sample of cells may be obtained from any of a number of different sources including, for example, bone marrow, fetal tissue (e.g., fetal liver tissue), peripheral blood, umbilical cord blood, pancreas, skin or any organ or tissue.

In a preferred embodiment, the CiLRCs are obtained from fibroblasts, neural derived stem cells, cells from the intestinal epithelium and adipose-derived stem cells. In a more preferred embodiment, CiLRCs are obtained from fibroblast, which can be neonatal (for example foreskin fibroblasts), newborn fibroblasts (i.e., fibroblasts obtained from a new born (post natal) organism) or adult fibroblast. In this embodiment, the newborn can be post natal day 1, day 2, day 3, day 4, day 5, day 6, day 7, day 8, day 9 or day 10, for example. In some preferred embodiment, the CiLRC cells do not express Oct4 and/or are not genetically engineered to express one or more markers of pluripotency.

Cells may be isolated by disaggregating an appropriate organ or tissue which is to serve as the cell source using techniques known to those skilled in the art. For example, the tissue or organ can be disaggregated mechanically and/or treated with digestive enzymes and/or chelating agents that weaken the connections between neighboring cells, so that the tissue can be dispersed to form a suspension of individual cells without appreciable cell breakage. Enzymatic dissociation can be accomplished by mincing the tissue and treating the minced tissue with one or more enzymes such as trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators.

D. Chemically Induced Lineage Reprogrammed Cells (CiLRCs)

CiLRCs possess a hybrid of properties which include properties of the cell of the first type from which they are obtained, and properties of the cells of the second type to which they are reprogrammed. CiLRCs show downregulation of genes characteristic of the lineage from which they are obtained, when compared to cells from that lineage, from the same organism. The gene can be downregulated by 2 fold, 3 fold, 4 fold, 5, fold, etc., or completely silenced. CiLRCs retain expression of one or more genes characteristic of the lineage from which they are obtained. Additionally, CiLRC attain increased expression of one or more genes characteristic of the lineage to which they are reprogrammed.

Preferably, the cells do not show increased expression of one or more ESC markers selected from nanog, Oct4, Dax1, Oct4, Nanog and Esrrb when compared to the cell of the first type from which it is obtained and the cells are not pluripotent.

Markers used to identify specific cell types are known in the art.

Neuronal Markers

Neurons possess certain known morphological and functional characteristics. Morphology characteristic of neurons includes for example, neurite outgrowth.

Neuronal-like morphology can be determined using well established methods, for example, microscopy, reviewed for example in Parekh, et al., *Neuron*, 77(6):1017-1038 (2013). Methods for quantifying neuronal morphology are described for example in Ho, et al., *BMC Bioinformatics*, 12:230 (2011). Neuron specific markers include TUJ1 (Neuron-specific class III beta-tubulin), MAP2, NF—H and NeuN. MAP-2 is a neuron-specific cytoskeletal protein that is used as a marker of neuronal phenotype. Izant, et al., *Proc Natl Acad Sci USA.*, 77:4741-5 (1980). NeuN is a neuronal specific nuclear protein identified by Mullen, et al., *Development*, 116:201-11 (1992). This protein, which they called Neuronal Nuclei (NeuN), was detected in most neuronal cell types throughout the central and peripheral nervous systems of adult mice.

Additional markers that may be used to identify neurons are reviewed for example in *Mater Methods*, 3:196 (2013). Excitatory or inhibitory membrane properties are evidenced by expression of neurotransmitter transporters such as vesicular glutamate transporter (vGlut) and/or Gad67 (glutamate decarboxylase 67), and membrane depolarization as measured in a patch-clamp assay. Glutamatergic neurons express at least one of three known vesicular glutamate transporters, VGLUT1, VGLUT2, or VGLUT3. These transporters mediate glutamate uptake into synaptic vesicles and are driven by a proton electrochemical gradient. The expression level of VGLUTs has been shown to determine the amount of glutamate loaded into vesicles and released, thereby regulating the efficacy of neurotransmission. Wojcik, et al., *PNAS*, 101(18:7158-7163 (2004). The inhibitory neurotransmitter γ-amino butyric acid (GABA) is synthesized by two isoforms of the enzyme glutamic acid decarboxylase (GAD): GAD65 and GAD67. In primary neurons, GAD67 is targeted to Golgi membranes, cytosolic vesicles, and presynaptic clusters independent of GAD65. Kanaani, et al., *J. Cell. Biol.*, 190(5):911-925).

CiLR Neurons

Chemically reprogrammed neurons show upregulation of one or more neuron-specific genes. For example the genes can be upregulated by 2 fold, 3 fold, 4 fold 5 fold or 6 fold. However, upregulation includes increased levels of expression of a gene considered a neuron-specific gene, when compared to the levels in the cell/cell type from which the CiLRs neuron was obtained. Preferred genes include enriched expression of one or more Further, CiLRs neuron can have similar membrane properties exhibited by neurons; these membrane properties are absent in the cells from which they are obtained.

The CiLRs neurons disclosed herein preferably do not include exogenously introduced nucleic acids that induce conversion of non-neuronal cells into neuron-like cells ("neurogenic nucleic acid"), introduced into the cell using genetic engineering techniques. Examples of neurogenic transcription factors and nucleotides include Ascl1, Zic1, Olig2, Brn2/4, NeuroD1 and Myt11 (Vierbuchen, et al., *Nature*, 463:1035-1041 (2010)); microRNAs (miRNAs) miR-9/9 or miR-124 (miR-9/9*-124) (Yoo, et al., *Nature*, 476(7359):228-31 (2011) and Ambasudhan, et al., *Cell Stem Cell*, 9(2):113-118 (2001); neurogenin 2 (NGN2); SOX11.

In a preferred embodiment, CiLR neurons show increased expression pan-neural genes (Mapt, Map2 and Nefl) and functional synaptic components (Stmn3, Stmn4 and Syp), whereas the expression of hallmark genes for the cells from which they are obtained, exemplified for fibroblasts to include Thy1, Twist2, Tgfb1i1 and Snail, are significantly downregulated. In another preferred embodiment endogenous expression of Sox2 in CiLR neurons is upregulated when compared to neuron-like cells produced by a method which includes culturing fibroblasts in cell culture medium containing the cocktail VC6TFAE for the same length of time in step (a) in the chemically induced reprogramming methods disclosed herein.

Fibroblast Markers

Exemplary fibroblast cell markers include Thy1 and/or up-regulation of SSEA-1. Fibroblast hallmark genes such as Fap, Des, Slug, Dcn, FSp1, Tgfb1i1, Snail, Collagen 1 and Twist2 are down-regulated in CiLR neurons.

Hepatocyte Markers

CiLR hepatocytes express one or more hepatocyte cell markers. hepatocyte cell markers include, but are not limited to albumin, Cytochrome P450 (Cyp)3A4, CYPB6, CYP1A2, CYP2C9, and/or CYP2C19; adipocyte markers include for example, adiponectin, fatty acid binding protein P4, and leptin. Morphological characterization of hepatocytes include the confirmation of morphological characteristics specific for hepatocytes such as cells having a plurality of nuclei observed by a phase microscope and granules rich in cytoplasm observed by an electron microscope, in particular, the presence of glycogen granules. Like CiLR neurons, the expression of hallmark genes for the cells from which they are obtained, exemplified for fibroblasts to include Thy1, Twist2, Tgfb1i1 and Snail, are significantly downregulated.

III. Methods of Making

The methods disclosed herein allow the chemical reprograming of a cell of a first type/linegae to a cell of a second cell type/lineage. The disclosed methods do not include transfecting the cell of a first type (for example, non-neuronal cell) with nucleic acids that induce conversion to cells of the second cell type (for example, neuron-like cells).

In one embodiment, the preferred cell of a second cell type is a neuron. In this embodiment, the method does not include transfecting the non-neuronal cell with nucleic acids that induce conversion of non-neuronal cells into neuron-like cells ("neurogenic nucleic acid"), introduced into the cell using genetic engineering techniques. Examples of neurogenic transcription factors and nucleotides include Ascl1, Zic1, Olig2, Brn2/4, NeuroD1 and Myt1l (Vierbuchen, et al., Nature, 463:1035-1041 (2010)); microRNAs (miRNAs) miR-9/9 or miR-124 (miR-9/9*-124) (Yoo, et al., Nature, 476(7359):228-31 (2011) and Ambasudhan, et al., Cell Stem Cell, 9(2):113-118 (2001); neurogenin 2 (NGN2); SOX11. The in a preferred embodiment does not include ISX9 [N-cyclopropyl-5-(2-thienyl)-3-isoxazolecarboxamide].

In another embodiment, the preferred cell of a second cell type is a hepatocyte. The method does not include transfecting the non-hepatocyte cell with nucleic acids that induce conversion of non-neuronal cells into hepatocyte-like cells.

The cells are plated at a starting cell density ranging from 10,000 cells/well to 70,000 cells/well, preferably between 30,000 and 60,000 cells/well and more preferably, about 25,000-30,000 cells/well for a 6 well plate.

A. Induction of CiLRCs Via Specific Selection of Conditions for a Modified XEN-Like State Bias Reprogramming cells of first type into cells of a second and different type/lineage via a modified XEN-like state bias includes the steps of (a) contacting the cell to be reprogrammed a first cocktail of CiLR (herein, modified XEN-Cocktail) for a sufficient period of time to bias the cells into a modified XEN-like cell population; and (b) culturing the population of modified XEN-like cells for a sufficient period of time to reprogram the cell into a cell of a second cell type/lineage (CiLRC) in lineage specific induction/differentiation cell culture media which includes compounds that bias the Xen-like cells towards the specific lineage (herein, Lineage specific media. The modified XEN cocktail is used to supplement cell culture media such as DMEM (Dulbecco's Modified Eagle Medium), knockout DMEM which are known in the art and are commercially available.

In a preferred embodiment, culture in the modified XEN-Cocktail results in upregulation of the endogenous expression of at least one lineage specifier for example, Sox2, Ngn2 and/or NeuroD1 expression is upregulated when compared to neuron-like cells produced by a method which includes culturing the cells of the first type in cell culture medium containing the cocktail VC6TFAE for the same length of time in step (a). Accordingly, the modified XEN-Cocktail is selected to include small molecules that increase expression of the lineage specifier.

In a preferred embodiment, cells to be reprogrammed are cultured initially in a modified XEN-Cocktail-containing medium for a total period preferably between 8 to 20 days, preferably from 10-16 days, more preferably, for 12 days (Stage 1). A preferred modified XEN-cocktail is V6TFAE-TD114-2. The cells are cultured in Lineage specific media from preferably, between 10-30 days (FIG. 1C), for examples between 20-24 days (Stage 2). In some embodiments, Forskolin is preferably present during the entire culture process and ISX9 is preferably not included in the cell culture medium of either Stage 1 or Stage 2. CHIR99021 and Dorsomorphin are preferably not included in step (a), although they can be included in step (b). Accordingly, a preferred cocktail for Stage (2) for producing CiLR neurons is FCD, which cocktail optionally includes LDN193189 and SB431542. A preferred cell culture medium for inducing hepatocytes from modified Xen-like cells includes DMEM 1% N2, 1% B27, 1% Glutamax, 1% penicillin/streptomycin (P/S), 20 ng/ml Activin A, 20 ng/ml EGF (epidermal growth factor), 20 ng/ml BMP4 (Bone morphogenic protein 4), and 10 ng/ml FGF2 (fibroblast growth factor 2). Xen-like cells are preferably cultured in this medium for a period ranging from 5-15 days, preferably between 8-10 day, and more preferably for about 10 days. This is followed by culture in modified HCM (Hepatocyte culture medium), 10 ng/ml OSM (Oncostatin M), 0.1 uM DEX (Dexamethasone) for a period ranging from 5-15 days, preferably between 8-10 days, and more preferably for about 10 days. However, factors which are known to induce and/or maintain hepatocyte growth can be used. As exemplified here for hepatocytes, one can apply known cell culture induction and differentiation media and culture conditions to the modified Xen-like cells disclosed herein to obtain different cell types. Lineage specific induction and differentiation media are known in the art and some are commercially available. For example, Banerrjee, et al. PLOS One, 7 (3) e33165 (2012) discloses cell culture media for differentiating human embryonic cells into lung epithelia lineage-specific cells. Cell culture in adipogenic, osteogenic, or chondrogenic medium is known and has previously been described. Mhanna, et al., Tissue engineering Part A. 201; 20 (7-8): 1165-74 (2014), Yang, et al., J. Biomed. Sci., 18, 59 (2011); Xi, et al., PLOS One DOI: 10.1371/journal. pone. 0145838 Jan. 12; 2016. (Liu, et el., Cell Res., 24 (10): 1181-1200 (2014). See also, Liu, et el., Cell Res., 24 (10): 1181-1200 (2014).

Inducing CiLRCs via a modified XEN-like state bias increases the efficiency of reprogramming. For example, the number of colonies obtained cells to be programmed are first biased towards a modified XEN-LIKE state from the same starting cell population is increased and/or the length of time it takes to obtain the same number of colonies is reduced when compared to a chemical reprograming method that does not selectively bias the cells to be programing towards a modified XEN-like state, and proceeds for example, by directly and immediately inducing the relevant transcription factors.

B. Isolation of CiLRCs

Media that can maintain the differentiated cells in in vitro culture are known.

A substantially purified population of CiLRCs can be obtained, for example, by extraction (e.g., via density gradient centrifugation and/or flow cytometry) from a culture source. Purity can be measured by any appropriate method. The CiLRC cells can be 99%-100% purified by, for example, flow cytometry (e.g., FACS analysis). Human CiLRC can be isolated by, for example, utilizing molecules (e.g., antibodies, antibody derivatives, ligands or Fc-peptide fusion molecules) that bind to a marker or a combination of markers on the CiLRC and thereby positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Antibodies may be conjugated with markers, such as magnetic beads, which allow for direct separation, biotin, which can be removed with avidin or streptavidin bound to a support, or fluorochromes, which can be used with a fluorescence activated cell sorter, to allow for ease of separation of the particular cell type. Any technique may be employed which is not unduly detrimental to the viability of the CiLRC. In one embodiment, the cells are incubated with an antibody against a marker and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest, the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, and Texas red.

Any cell type-specific markers can be used to select for or against a particular cell type. Induced stem cell markers useful for enrichment comprise expressed markers such as TRA-1-81 and loss of markers (e.g., GFP) associated with a retroviral vector or other exogenous vector.

C. Culture and Preservation of CiLRCs

The CiLRCs can be expanded in culture and stored for later retrieval and use. Once a culture of cells is established, the population of cells is mitotically expanded in vitro by passage to fresh medium as cell density dictates, under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor). Cultured cells can be transferred to fresh medium when sufficient cell density is reached. Cell culture medium for maintaining neuronal cells are commercially available.

Cells can be cryopreserved for storage according to known methods, such as those described in Doyle, et al., (eds.), 1995, Cell & Tissue Culture: Laboratory Procedures, John Wiley & Sons, Chichester. For example, cells may be suspended in a "freeze medium" such as culture medium containing 15-20% fetal bovine serum (FBS) and 10% dimethylsulfoxide (DMSO), with or without 5-10% glycerol, at a density, for example, of about $4\text{-}10 \times 10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years.

IV. Methods of Use

The approach of lineage reprogramming has been used in disease modeling, suggesting promising applications in regenerative medicine (Xu, et al., *Cell Stem Cell,* 16:119-134 (2015)). Cell-based therapy is seeing application in human clinical trials. For example, Geron Corporation and SanBio, Inc. have carried out clinical trials for human embryonic stem cell-based and bone marrow derived cells, respectively, in neuronal disorders. Therefore, the cells disclosed herein can be used in cell-based therapies.

Additionally, the discovery of the plasticity of a chemically induced XEN-like state makes it useful in a method of screening small molecule libraries for compounds that can enhance endogenous expression of lineage specifiers, providing small molecule cocktails useful for inducing a modified XEN-like state with increased expression of the lineage specifier, useful for subsequent induction into the desired lineage.

A. Cell Therapy

Therapeutic uses of the CiLRC include transplanting the CiLRC into individuals to treat a variety of pathological states including diseases and disorders resulting from cancers, wounds, neoplasms, injury, viral infections, diabetes and the like. Treatment may entail the use of the cells to produce new tissue, and the use of the tissue thus produced, according to any method presently known in the art or to be developed in the future. The cells may be implanted, injected or otherwise administered directly to the site of tissue damage so that they will produce new tissue in vivo. In one embodiment, administration includes the administration of genetically modified CiLRCs.

In a preferred embodiment, the CiLRCs are obtained from autologous cells i.e., the donor cells are autologous. However, the cells can be obtained from heterologous cells. In one embodiment, the donor cells are obtained from a donor genetically related to the recipient. In another embodiment, donor cells are obtained from a donor genetically un-related to the recipient.

If the human CiLRCs are derived from a heterologous (non-autologous/allogenic) source compared to the recipient subject, concomitant immunosuppression therapy is typically administered, e.g., administration of the immunosuppressive agent cyclosporine or FK506. Alternatively, the cells can be encapsulated in a membrane, which permits exchange of fluids but prevents cell/cell contact. Transplantation of microencapsulated cells is known in the art, e.g., Balladur et al., *Surgery*, 117:189-94, 1995; and Dixit et al., *Cell Transplantation*, 1:275-79 (1992).

(i) Diabetes

Diabetes mellitus (DM) is a group of metabolic diseases where the subject has high blood sugar, either because the pancreas does not produce enough insulin, or, because cells do not respond to insulin that is produced. A promising replacement for insulin therapy is provision of islet cells to the patient in need of insulin. Shapiro et al., *N Engl J Med.*, 343(4):230-8 (2000) have demonstrated that transplantation of beta cells/islets provides therapy for patients with diabetes. Although numerous insulin types are commercially available, these formulations are provided as injectables. The CiLRCs disclosed herein can provide an alternative source of islet cells to prevent or treat diabetes. Accordingly, the cells are useful for transplantation in order to prevent or treat the occurrence of diabetes. Methods for reducing inflammation after cytokine exposure without affecting the viability and potency of pancreatic islet cells are disclosed for example in U.S. Pat. No. 8,637,494 to Naziruddin, et al.

(ii) Neurodegenerative Disorders

Neurodegenerative disorders are characterized by conditions involving the deterioration of neurons as a result of disease, hereditary conditions or injury, such as traumatic or ischemic spinal cord or brain injury. Neurodegenerative conditions include any disease or disorder or symptoms or causes or effects thereof involving the damage or deterioration of neurons. Neurodegenerative conditions can include, but are not limited to, Alexander Disease, Alper's Disease, Alzheimer Disease, Amyotrophic Lateral Sclerosis, Ataxia Telangiectasia, Canavan Disease, Cockayne Syndrome, Corticobasal Degeneration, Creutzfeldt-Jakob Disease, Huntington Disease, Kennedy's Disease, Krabbe Disease, Lewy Body Dementia, Machado-Joseph Disease, Multiple Sclerosis, Parkinson Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes Dorsalis or any other condition associated with damaged neurons. Other neurodegenerative conditions can include or be caused by traumatic spinal cord injury, ischemic spinal cord injury, stroke, traumatic brain injury, and hereditary conditions.

In particular, the disclosed methods include transplanting into a subject in need thereof CiLR neurons that have been expanded in vitro such that the cells can ameliorate the neurodegenerative condition. Transplantation of the expanded neuron-like cells can be used to improve ambulatory function in a subject suffering from various forms of myelopathy with symptoms of spasticity, rigidity, seizures, paralysis or any other hyperactivity of muscles. Methods for expanding and transplanting neural cells and neural progenitor cells for the treatment of different neurodegenerative conditions is disclosed for example, in U.S. Pat. No. 8,236,299 to Johe, et. al.

(iii) Hepatic Disorders

Liver failure and loss of function is one of the most severe consequences of liver disease. Because of its rapid onset, rapid progression, liver transplantation is the primary means of treatment of these diseases. However, donor scarcity presents a serious lack of many patients dying while waiting for liver transplantation. CiLR hepatocytes can be transplanted into a recipient organism using a carrier such as a matrix that known for transplantation of hepatocytes. For example, Zhou, et al., *Liver Transpl.*, 17(4):418-27 (2011) discloses the use of decellularized liver matrix (DLM) as a carrier for hepatocyte transplantation. Methods for isolating liver and pancreas cells from tissue samples, seeded onto a poly-L-lactic acid matrix and re-implanted into the mesentery of the same patient are known in the art.

CiLR hepatocytes can also be used in the bio-artificial liver support systems. Bioartificial liver support systems based on the disclosed cells are constructed to temporarily replace the main function of liver failure (remove of hazardous substances, provide the liver synthetic biologically active substances), to stabilize and improve the patient's internal environment, until a suitable donor source for transplantation. Methods for making bioartifical liver are disclosed for example in U.S. Publication No. 2008/0206733.

(iv) Cancer Therapy

Therapeutic uses of the CiLRCs and their progeny include transplanting the cells into individuals to treat and/or ameliorate the symptoms associated with cancer. For example, in one embodiment, the CiLRCs can be administered to cancer patients who have undergone chemotherapy that has killed, reduced, or damaged cells of a subject. In a typical stem cell transplant for cancer, very high doses of chemotherapy are used, often along with radiation therapy, to try to destroy all the cancer cells. This treatment also kills the stem cells in the bone marrow. Soon after treatment, stem cells are given to replace those that were destroyed.

In another embodiment, the CiLRCs can be transfected or transformed (in addition to the de-differentiation factors) with at least one additional therapeutic factor. For example, once CiLRCs are isolated, the cells may be transformed with a polynucleotide encoding a therapeutic polypeptide and then implanted or administered to a subject, or may be differentiated to a desired cell type and implanted and delivered to the subject. Under such conditions the polynucleotide is expressed within the subject for delivery of the polypeptide product.

(v) Tissue Engineering

CiLRCs and their progeny can be used to make tissue engineered constructions, using methods known in the art. Tissue engineered constructs may be used for a variety of purposes including as prosthetic devices for the repair or replacement of damaged organs or tissues. They may also serve as in vivo delivery systems for proteins or other molecules secreted by the cells of the construct or as drug delivery systems in general. Tissue engineered constructs also find use as in vitro models of tissue function or as models for testing the effects of various treatments or pharmaceuticals. The most commonly used biomaterial scaffolds for transplantation of stem cells are reviewed in the most commonly used biomaterial scaffolds for transplantation of stem cells is reviewed in Willerth, S. M. and Sakiyama-Elbert, S. E., *Combining stem cells and biomaterial scaffolds for constructing tissues and cell delivery* (Jul. 9, 2008), StemBook, ed. The Stem Cell Research Community, StemBook. Tissue engineering technology frequently involves selection of an appropriate culture substrate to sustain and promote tissue growth. In general, these substrates should be three-dimensional and should be processable to form scaffolds of a desired shape for the tissue of interest.

U.S. Pat. No. 6,962,814 generally discloses method for producing tissue engineered constructs and engineered native tissue. With respect to specific examples, U.S. Pat. No. 7,914,579 to Vacanti, et al., discloses tissue engineered ligaments and tendons. U.S. Pat. No. 5,716,404 discloses methods and compositions for reconstruction or augmentation of breast tissue using dissociated muscle cells implanted in combination with a polymeric matrix. U.S. Pat. No. 8,728,495 discloses repair of cartilage using autologous dermal fibroblasts. U.S. Published application No. 20090029322 by Duailibi, et al., discloses the use of stem cells to form dental tissue for use in making tooth substitute. U.S. Published application No. 2006/0019326 discloses cell-seed tissue-engineered polymers for treatment of intracranial aneurysms. U.S. Published application No. 2007/0059293 by Atala discloses the tissue-engineered constructs (and method for making such constructs) that can be used to replace damaged organs for example kidney, heart, liver, spleen, pancreas, bladder, ureter and urethra.

The CiLRCs can be formulated for administration, delivery or contacting with a subject, tissue or cell to promote de-differentiation in vivo or in vitro/ex vivo. Additional factors, such as growth factors, other factors that induce differentiation or dedifferentiation, secretion products, immunomodulators, anti-inflammatory agents, regression factors, biologically active compounds that promote innervation, vascularization or enhance the lymphatic network, and drugs, can be incorporated.

The CiLRC can be administered to a patient by way of a composition that includes a population of CiLRCs alone or on or in a carrier or support structure. In many embodiments, no carrier will be required. The cells can be administered by injection onto or into the site where the cells are required. In these cases, the cells will typically have been washed to remove cell culture media and will be suspended in a physiological buffer.

In other embodiments, the cells are provided with or incorporated onto or into a support structure. Support structures may be meshes, solid supports, scaffolds, tubes, porous structures, and/or a hydrogel. The support structures may be biodegradable or non-biodegradable, in whole or in part. The support may be formed of a natural or synthetic polymer, metal such as titanium, bone or hydroxyapatite, or a ceramic. Natural polymers include collagen, hyaluronic acid, polysaccharides, and glycosaminoglycans. Synthetic polymers include polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters. These may be in for the form of implants, tubes, meshes, or hydrogels.

Solid Supports

The support structure may be a loose woven or non-woven mesh, where the cells are seeded in and onto the mesh. The structure may include solid structural supports. The support may be a tube, for example, a neural tube for regrowth of neural axons. The support may be a stent or valve. The support may be a joint prosthetic such as a knee or hip, or part thereof, that has a porous interface allowing ingrowth of cells and/or seeding of cells into the porous structure. Many other types of support structures are also possible. For example, the support structure can be formed from sponges, foams, corals, or biocompatible inorganic structures having internal pores, or mesh sheets of interwoven polymer fibers. These support structures can be prepared using known methods.

The support structure may be a permeable structure having pore-like cavities or interstices that shape and support the hydrogel-cell mixture. For example, the support structure can be a porous polymer mesh, a natural or synthetic sponge, or a support structure formed of metal or a material such as bone or hydroxyapatite. The porosity of the support structure should be such that nutrients can diffuse into the structure, thereby effectively reaching the cells inside, and waste products produced by the cells can diffuse out of the structure The support structure can be shaped to conform to the space in which new tissue is desired. For example, the support structure can be shaped to conform to the shape of an area of the skin that has been burned or the portion of cartilage or bone that has been lost. Depending on the material from which it is made, the support structure can be shaped by cutting, molding, casting, or any other method that produces a desired shape. The support can be shaped either before or after the support structure is seeded with cells or is filled with a hydrogel-cell mixture, as described below.

An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape. Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Hydrogels

In another embodiment, the cells are mixed with a hydrogel to form a cell-hydrogel mixture. Hydrogels may be administered by injection or catheter, or at the time of implantation of other support structures. Crosslinking may occur prior to, during, or after administration.

B. Screening Methods

Screening systems and methods for identifying an agent that biases cells in a XEN-like state to a particular lineage (modified XEN-like state), which can be subsequently induced to that lineage.

The method includes screening small molecule libraries to identify replacements for the molecules used to chemically induce a XEN-like state (VC6TFAE) that would increase expression of lineage determinant genes, preferably at least one gene from each of the three germ layers in a target cell, for example, a fibroblast. Development following fertilization proceeds via the formation of three germ layer, the ectoderm, endoderm and mesoderm. The ectoderm develops into the surface ectoderm, neural crest, and the neural tube. The surface ectoderm develops into: epidermis, hair, nails, lens of the eye, sebaceous glands, cornea, tooth enamel, the epithelium of the mouth and nose. The neural crest of the ectoderm develops into: peripheral nervous system, adrenal medulla, melanocytes, facial cartilage, dentin of teeth. The neural tube of the ectoderm develops into: brain, spinal cord, posterior pituitary, motor neurons, retina. The mesoderm forms: muscle (smooth and striated), bone, cartilage, connective tissue, adipose tissue, circulatory system, lymphatic system, dermis, genitourinary system, serous membranes, and notochord. The endoderm forms the epithelial lining of the most of the digestive tract. It also forms the lining cells of all the glands which open into the digestive tube.

The method disclosed herein can be used to identify agents that can be used to bias XEN-like cells towards expression of genes governing cell fates towards three germ layers.

Genes that function as lineage specifiers are known in the art, and include for example, GATA3, GATA6, and SOX7, which are involved in mesendodermal (ME) lineage specification; the ectodermal lineage specifiers Dlx3, GMN1V; Additional lineage specifiers include Oct4, Sox2, Gata4, Pax1, CEBPα, GRB2, ASCL1, MIXL1, Sox1, Sox3, and RCOR2 andHnf4a (Shu, et al., *Cell*, 153:963-975 (2013)). Specifically, neuroectormal markers include Neuroectoderm genes: Sox2, Msl1, Nefl; NefH, Pax3, Pax6 and neurog2; Mesoderm genes: Msx1, Smn1, Lmo2 Eomes, Bmps, Msx2; and Endoderm genes: Hnf1b, Krt8, Gata4, Sox17, Krt18, Foxa2, cdh1, Cdx2, and Gata6.

V. Kits

Kits are provided which include the chemical inducers of lineage reprogramming (CiLR) disclosed herein. The CiLR are as described above. These may be in a form having defined concentrations to facilitate addition to cell culture media to produce a desired concentration. The kit may include directions providing desired concentration ranges and times of administration based on the types of cells to be induced. The kit may also include cell culture media which is pre-mixed with the CiLR for culture of cells to induce lineage reprogramming.

The present invention will be further understood by reference to the following non-limiting examples.

Examples

Materials and Methods
Mice

TauEGFP knock-in mice, Fsp1-Cre transgenic mice and Rosa26-loxp-STOP-loxp-tdTomato mice were performed as previously reported (Li et al., *Cell Stem Cell*, 17:195-203 (2015)). Oct4-CreER mice (stock number 016829) were from Jackson Laboratory and were crossed with Rosa26-lox-STOP-lox-tdTomato mice to prepare fibroblasts for tracing Oct4 as previously reported (Bar-Nur et al., *Nat Biotechnol.*, 33:761-768 (2015)). All animal experiments were performed according to the Animal Protection Guidelines of Peking University, China.

Cell Culture

Fibroblasts were isolated and prepared as previously described (Li et al., *Cell Stem Cell*, 17:195-203 (2015)) and cultured in DMEM (Gibco) supplemented with 10% FBS (Pan-Biotech), 1% GlutaMAX™-I (Invitrogen), 1% NEAA (Invitrogen), 0.055 mM β-ME (Sigma). Mouse ESCs and iPSCs were cultured on feeder layers of mitomycin C-treated MEFs in ESC culture medium containing KnockOut DMEM (Invitrogen), 10% KSR (Invitrogen), 10% FBS (Pan-Biotech), 1% GlutaMAX™-I (Invitrogen), 1% NEAA (Invitrogen), 0.055 mM β-ME (Sigma), 1% penicillin-streptomycin (Invitrogen) and 1,000 U/ml leukemia inhibitory factor (LIF, Miltenyi Biotec) and 2i (3 μM CHIR99021 and 1 μM PD0325901).

Detailed Protocol for Chemically Inducing Neurons from Fibroblasts
Small Molecules Preparation Small molecules used in this study, including: VPA, TD114-2, 616452, Tranylcypromine, Forskolin, AM580, EPZ004777 and others, were listed in details (Table 1). The small molecule compounds were prepared as previously reported (Zhao et al., *Cell*, 163:1678-1691 (2015)). TD114-2 was synthesized according to the chemical structure (Kuo et al., *J. Med. Chem.*, 6, 4021-4031 (2003)).

TABLE 1

Small Molecules Used in This Study; and related to FIG. 1

| Full Name | Abbreviation | Dose (uM) | Source |
|---|---|---|---|
| VPA | V | 500 | Sigma, cat. no. P4543 |
| CHIR99021 | C | 10-20 | Synthesized by WUXI APPTEC |
| 616452 | 6 | 10 | Synthesized by WUXI APPTEC |
| Tranylcypromine | T | 5 | Enzo, cat. no. BML-EI217-0005 |
| Forskolin | F | 10-50 | Enzo, cat. no. BML-CN100-0100 |
| AM580 | A | 0.05 | Tocris, cat. no. 0760 |
| EPZ004777 | E | 5 | Selleckchem, cat. no. S7353 |
| TD114-2 | TD114-2 | 2-4 | Synthesized by WUXI APPTEC |
| Dorsomorphin | D | 1-2 | Tocris, cat. no. 3093 |
| LDN193189 | L | 0.1 | Selleckchem, cat. no. S2618 |
| SB431542 | S | 2-10 | Tocris, cat. no. 1614 |

Culture Medium Preparation

Stage 1 culture medium preparation: KnockOut DMEM (Invitrogen) supplemented with 10% KSR (Invitrogen), 10% FBS (Pan-Biotech), 1% GlutaMAX™-I (Invitrogen), 1% NEAA (Invitrogen), 0.055 mM β-ME (Sigma), 1% penicillin-streptomycin (Invitrogen), 100 ng/ml bFGF (Origene) containing the small-molecule cocktail: 0.5 mM VPA, 2-4 μM TD114-2 or 20 μM CHIR, 10 μM 616452, 10 μM Tranylcypromine, 10-50 μM Forskolin, 0.05 μM AM580 and 5 μM EPZ004777 (VT6TFAE or VC6TFAE). For mouse adult lung fibroblasts (MAFs) induction, 1 μM CH55 and 50 μg/ml Vitamin C (VC) were added enhance the induction efficiency.

Stage 2 culture medium preparation: Neurobasal (Invitrogen) with 0.5% N-2 (Invitrogen), 1% B-27 (Invitrogen), 1% GlutaMAX™-I (Invitrogen), 1% penicillin-streptomycin (Invitrogen), 25 ng/ml bFGF, 20 ng/ml BDNF, 20 ng/ml GDNF containing the small-molecule cocktail: 10-50 μM forskolin, 3 μM CHIR, 1 μM Dorsomorphin (FCD), (0.1 μM LDN193189 and 5 μM SB431542, which are not essential to induce neurons but are favorable to enhance the induction efficiency).

Chemically Induce Neurons from Fibroblasts

TauEGFP fibroblasts were prepared as previously reported (Li et al., *Cell Stem Cell,* 17:195-203 (2015)). Fibroblasts were seeded at a density of 30,000-50,000 cells per well of a 6-well plate or 300,000 cells per 100 mm dish (day −1) (Fibroblast medium–DMEM basal medium+10% FBS++beta-Me(0.055 mM)+1% PS). The culture plates or dishes were precoated with 0.1% gelatin.

The medium was changed to Stage 1 culture medium (Day 0). For stage 1 chemical reprogramming, cells were induced by the culture medium containing 0.5 mM VPA, 2-4 μM TD114-2 or 20 μM CHIR, 10 μM 616452, 10 μM Tranylcypromine, 10-50 μM Forskolin, 0.05 μM AM580 and 5 μM EPZ004777(VT6TFAE or VC6TFAE)) for 12 days. Culture medium was refreshed every 4 days during the inducing period. XEN-like colonies were formed at about day 6-8.

On day 12, cells were switched into stage 2 neural specification medium. After 8-12 days induction by the stage 2 culture medium, TauEGFP-positive colonies were generated. The TauEGFP-positive colonies were further re-plated to co-culture with primary astrocytes or primary neurons for maturation.

Optional Step: XEN-like colonies at the end of stage 1 was compact. Operating a re-plating step on day 12 can expand the XEN-like colonies and enhance the yields of neurons.

Trypsinize and re-plate the cells at a density of 10,000-200,000 cells per well of a 6-well plate in stage 1 culture medium. XEN-like colonies were reformed 4-6 days after being re-plated and then were switched into stage 2 neural induction medium. After 8-12 days in stage 2 medium, XEN-like colonies become TauEGFP-positive. Extending the inducing period can generate more TauGFP-positive colonies and enhance the maturity, as revealed by the development of neurite-like growth. These TauEGFP-positive cells can be subjected to characterization or replated to co-culture with primary astrocytes or primary neurons for further maturation.

Primary Neurons Culture, Primary Astrocytes Culture and Co-Culture

Primary culture of neurons was carried out as previously described (Li et al., *Cell Stem Cell,* 17:195-203 (2015)). Primary astrocytes were isolated from postnatal day 1 wild-type ICR mice. After disinfection, the mice were decapitated. Their cerebra and hippocampus were removed into pre-cooled PBS (Gibco). Remove the meningeal and cut up the remnant tissues. The debris of the tissue were digested with 2 ml 0.25% trypsin (Gibco, dissolved in digestion solution) for 20 min, then the digestion was stopped with 2 ml Dulbecco's Modified Eagle Medium/F12 (DMEM) medium (Gibco) containing 10% FBS (Gibco). The cells were centrifuged for 5 min at 1500 rpm and were resuspended in DMED/F12 medium, a total of 6×105 cells were plated onto 100 mm culture dish for 30 min. After that, supernatant was sucked out and put into 25 cm2 culture flask coated with 12.5 μg/ml poly-D-lysine. The flask was incubated at 37° C. in a 5% CO2/95% air. Refresh the medium every 3 days. At day 10, shake the flask in the shaking table at 260 rpm for 18 h to remove the Microglia cells. One week after isolating of primary neurons and astrocytes, the TauEGFP-positive colonies trypsinized and replated onto primary neurons or astrocytes for further maturation.

Doubling Time Analysis

The cell numbers of ES cells, fibroblasts, CeXEN cells and XEN-like cells at different passages were determined by counting every eight hours (n=3). The growth curves of these cells were fitted by linear regression with normalization to the starting cell density. The doubling time was calculated as doubling time=ln (2)/growth rate for each time window analyzed.

XEN-Like Cells Passaging and Expanding

Day 12 induced)(EN-like colonies (P0) were trypsinized from whole well and re-plated onto gelatin-coated culture plates at a ratio of 1:10-20 in stage 1 medium for the first passage. After the)(EN-like cells at Passage 1 become confluence, passage the cells at a ratio of 1:20-30 every 3-4 days in stage 1 medium. The XEN-like cells can be long term expanded at stage 1 medium for more than 20 passages with lineage specifying potentials.

For a single primary XEN-like colony passaging, feeder layers of mitomycin C-treated MEFs are needed. Pick up the a single primary XEN-like colony with 1 ml syringe, trypsinize for 5 min, and neutralize with stage 1 culture medium, then pipette up and down to obtain a single-cell suspension. Seed the cell suspension on feeder layers with stage 1 culture medium for further expansion. The subsequent passaging of XEN-like cells can be feeder-free.

For neural induction from passaged XEN-like cells, cells were plated at 50,000-100,000 cells per well of a 6-well plate (with gelatin-coated) in stage 1 medium (day 0). Until passaged cells become 70-80% confluence on day2 or day3, switch the XEN-like cells into stage 2 neural induction medium. After 12-20 days, TauEGFP-positive colonies emerged.

Notes:

A relatively low initial cell density is beneficial for neural induction from passaged XEN-like cells since the high proliferation rate of XEN-like cells.

Considering that FSK used at high concentration 50 μM was toxic to passaged XEN-like cells at stage 2, a concentration of 10-20 μM in neural induction culture medium on passaged XEN-like cells is preferred.

Generation of Neurons from CeXEN Cell Lines

CeXEN (chemically-derived eXEN) cells with TauEGFP reporter were derived from E3.5 blastocysts using stage 1 culture medium as previously reported (Zhao et al., *Cell,* 163:1678-1691 (2015)). Medium was changed every day and the cells were passaged at 1:20 to 1:30 every 3 days.

1. For chemical induction, CeXEN cells were plated at 50,000-100,000 cells per well of a 6-well plate (with gelatin-coated) in stage 1 medium (day 0).

2. On day2 or day3 until 70-80% confluence, cells were switched into stage 2 neural induction culture medium for 12-20 days and TauEGFP-positive cells were generated.

A relatively low initial cell density is beneficial for lineage induction from passaged CeXEN cells since the high proliferation rate of CeXEN cells. Considering that FSK used at high concentration 50 μM was toxic to CeXEN cells at stage 2, a concentration of 10-20 μM in neural induction culture medium on CeXEN cells is preferred.

Immunofluorescence

Immunofluorescence was carried out as previously described (Li et al., *Cell Stem Cell,* 17:195-203 (2015)). For Immunofluorescence, Primary antibodies included those specific to TUJ1 (Covance, rabbit anti, 1:500), TUJ1 (Santa Cruz, mouse anti, 1:100), MAP2 (Sigma-Aldrich, mouse anti, 1:200), NF-H (Abcam, rabbit anti, 1:500), SYN(Abcam, rabbit anti, 1:500), NEUN (Millipore, mouse anti, 1:100), vGLUT1 (Synaptic Systems, rabbit anti, 1:5,000), GABA (Sigma-Aldrich, rabbit anti, 1:5,000), OCT4 (Abcam, rabbit anti, 1:200), NANOG (Abcam, rabbit anti, 1:200), SALL4 (Abcam, rabbit anti, 1:500), SOX17 (R&D, goat anti, 1:500), GATA4 (Santa Cruz, goat anti, 1:100), GATA6 (R&D, goat anti, 1:200), AFP (Santa Cruz, mouse anti, 1:200), ALB (Abcam, goat anti, 1:500). Secondary antibodies used in this study including: 488-conjugated secondary antibodies, Cy3-conjugated secondary antibodies and 647-conjugated secondary antibodies (Jackson ImmunoResearch).

qRT-PCR

Total RNA was extracted using the Direct-Zol™ RNA Kit (Zymo Research) and was reverse transcribed into cDNA using TransScript One-step gDNA Removal and cDNA Synthesis SuperMix (TransGen Biotech). Real-time PCR was carried out using KAPA SYBR® FAST qPCR Kit Master Mix (KAPA Biosystems) and performed on a CFX Connect™ Real-Time System (Bio-Rad). The primers used in this study were listed in Table 2. Data was analyzed using the ΔΔCt method. All the results were normalized to Gapdh expression, and the values of fibroblasts were set to 1. Two replicates were used to determine the error bars.

TABLE 2

Primers used for real-time qPCR

| GENE NAME | FORWARD (5' TO 3') | REVERSE (5' TO 3') |
|---|---|---|
| Gapdh | CATGTTCCAGTATGACTCCACTC (SEQ ID NO: 1) | GGCCTCACCCCATTTGATGT (SEQ ID NO: 2) |
| Sox2 | CGGGAAGCGTGTACTTATCCTT (SEQ ID NO: 3) | GCGGAGTGGAAACTTTTGTCC (SEQ ID NO: 4) |
| Oct4 | CAGGGCTTTCATGTCCTGG (SEQ ID NO: 5) | AGTTGGCGTGGAGACTTTGC (SEQ ID NO: 6) |
| Esrrb | GTGGCTGAGGGCATCAATG (SEQ ID NO: 7) | AACCGAATGTCGTCCGAAGAC (SEQ ID NO: 8) |
| Nanog | AGTTATGGAGCGGAGCAGCAT (SEQ ID NO: 9) | AGGCCTGGACCGCTCAGT (SEQ ID NO: 1) |
| Gata6 | TGAGGTGGTCGCTTGTGTAG (SEQ ID NO: 11) | ATGGCGTAGAAATGCTGAGG (SEQ ID NO: 12) |
| Gata4 | GAGCTGGCCTGCGATGTCTGAGTG (SEQ ID NO: 13) | AAACGGAAGCCCAAGAACCTGAAT (SEQ ID NO: 14) |
| Sox17 | GTCAACGCCTTCCAAGACTTG (SEQ ID NO: 15) | GTAAAGGTGAAAGGCGAGGTG (SEQ ID NO: 16) |
| Ascl1 | ACTTGAACTCTATGGCGGGTT (SEQ ID NO: 17) | CCAGTTGGTAAAGTCCAGCAG (SEQ ID NO: 18) |
| Brn2 | GACAAGATCGCAGCGCAAGG (SEQ ID NO: 19) | GGCTTAGGGCATTTGAGGAA (SEQ ID NO: 20) |
| NeuroD1 | ACGCAGAAGGCAAGGTGTCC (SEQ ID NO: 21) | GTTCCTCGTCCTGAGAACTG (SEQ ID NO: 22) |
| Ngn2 | TGGCTGGCATCTGCTCTATT (SEQ ID NO: 23) | TAGGCATTGTGACGAATCTG (SEQ ID NO: 24) |
| Col1a1 | CATGTTCAGCTTTGTGGACCT (SEQ ID NO: 25) | GCAGCTGACTTCAGGGATGT (SEQ ID NO: 26) |

TABLE 2-continued

Primers used for real-time qPCR

| GENE NAME | FORWARD (5' TO 3') | REVERSE (5' TO 3') |
|---|---|---|
| Fsp1 | GTGTCCACCTTCCACAAATACTCA (SEQ ID NO: 27) | ACTTCATTGTCCCTGTTGCTGTC (SEQ ID NO: 28) |
| Cyp2a5 | GCACTTCCTAGATGACAAGGGACA (SEQ ID NO: 29) | CAGGCTCAACGGGACAAGAA (SEQ ID NO: 30) |
| Hnf4a | CATCACCACCATCGTCAA (SEQ ID NO: 31) | CCTCGTGTCACATCTTCTT (SEQ ID NO: 32) |
| Alb | ATGTTACCAAGTGCTGTAGT (SEQ ID NO: 33) | AATCTGCTTCTCCTTCTCTG (SEQ ID NO: 34) |
| Afp | TTCCTGTCTCAGTCATTCTAAG (SEQ ID NO: 35) | AGTCTCCTAAGGTCTGGTAG (SEQ ID NO: 36) |
| Cyp3a11 | TACTGTGATGGAGATGGAATAC (SEQ ID NO: 37) | GGTGAAGAGCATAAGATGGA (SEQ ID NO: 38) |
| Ttr | CTCACCACAGATGAGAAG (SEQ ID NO: 39) | GGCTGAGTCTCTCAATTC (SEQ ID NO: 40) |
| Hnf6a | AAATAAGCGTCCGTCCAAAGAA (SEQ ID NO: 41) | GACGATGAACTGCCTGAGTTG (SEQ ID NO: 42) |
| Cyp3a13 | AGTGCTGGTGAAGGAATG (SEQ ID NO: 43) | CTGGTGAAGGTTGGAGAC (SEQ ID NO: 44) |
| Cyp2b10 | GTCCATCCTCCAGAACTTC (SEQ ID NO: 45) | TTCCAATACCACTCTCCTTG (SEQ ID NO: 46) |
| Gjb1 | CGTGAATCGGCACTCTACAGC (SEQ ID NO: 47) | TGCACCTTGTGTCTCTTTACCCTC (SEQ ID NO: 48) |
| Sult1a1 | AACATGGAGCCCTTGCGTAAA (SEQ ID NO: 49) | ATGAGCACATCATCAGGCCAG (SEQ ID NO: 50) |
| Gstt1 | AGGCTCGTGCTCGTGTAGA (SEQ ID NO: 51) | CAGGGAACATCACCTTATGCC (SEQ ID NO: 52) |
| Actin | CGCCACCAGTTCGCCATGGA (SEQ ID NO: 53) | TACAGCCCGGGGAGCATCGT (SEQ ID NO: 54) |

RNA-Seq

Total RNA was isolated using the RNeasy Plus Mini Kit (Qiagen). RNA sequencing libraries were constructed using the NEBNext® Ultra™ RNA Library Prep Kit for Illumina® (NEB). Fragmented and randomly primed 2×100 bp paired-end libraries were sequenced using Illumina HiSeq 2500. The RPKM values were used to evaluate the expression levels of genes. The hierarchical clustering was conducted by Cluster 3.0 and TreeView. In the scatter plot, a 2 fold-change threshold cutoff was set for analysis. Gene ontology analysis of the DE genes was performed using the DAVID program.

Electrophysiology

Whole-cell patch clamp recordings were performed as previously described (Li et al., *Cell Stem Cell*, 17:195-203 (2015)). The artificial cerebrospinal fluid extracellular solution contained (in mM) 141 NaCl, 2.5 KCl, 1.3 MgCl2, 2.4 CaCl2, 1.25 NaH2PO4, 10 glucose and 10 HEPES, the pH was adjusted to 7.4 with NaOH. Patch pipettes were pulled (~5 MΩ tip resistance) with a P97 micropipette puller (Sutter Instruments) filled with internal pipette solution contained (in mM) 140 potassium gluconate, 1 CaCl2, 10 EGTA, 2 MgCl2, 5 Na2ATP, and 10 HEPES, the pH was adjusted to 7.4 with KOH. Patch-clamp recordings were taken using an EPC-10 amplifier (HEKA) with PatchMaster. Cell membrane potentials were held typically at −80 mV and depolarized to test potentials from −80 to +80 mV in 10 mV increments to record the sodium and potassium currents. The sample was 20 μs and sweep intervals were 2 s. For current-clamp recordings, a hyperpolarized current was injected into chemical neurons to membrane potentials around −70 mV. Action potentials were elicited by step-depolarized currents with sweep intervals of 3 s. The cells were held at 0 pA to record the resting membrane potentials. In current-clamp mode, the sample frequency was 25 kHz. Induced neurons identified by GFP were co-cultured with mouse primary astrocytes to record spontaneous excitatory postsynaptic currents (sEPSCs) or spontaneous inhibitory postsynaptic currents (sIPSCs). The induced neurons were held at a holding potential of −70 mV (close to the reversal potential of chloride) and 0 mV, respectively. The data were continuously digitized at 20 kHz. For neurotransmitter response, Glutamate (100 μM, Sigma-Aldrich) was dissolved in ACSF, loaded into a pipette, and puffed onto hciN cells using a picosprizer III (Parker Instrument) with 10 psi and is duration. All recordings were conducted at room temperature.

For brain slice recording, mice brains were dissected quickly and placed in ice-cold oxygenated artificial CSF (aCSF) containing the following (in mM): 125 NaCl, 2.5 KCl, 2 CaCl2, 2 Mgcl2-6H2O, 1.25 NaH2PO4-2H2O, 25 NaHCO$_3$ and 10 glucose, at pH 7.4. Coronary slices of 300 mm thick were made with a vibratome (VT-1200S; Leica) and were maintained in an incubation chamber with oxygenated (95% O2/5% CO2) aCSF at 37° C. for 15 min and then transferred to room temperature for 30 min before being transferred to the recording chamber.

Karyotype and Comparative Genomic Hybridization (CGH) Analysis—

Karyotype analyses were performed as previously described. For CGH experiments, genomic DNA was extracted and hybridized to NimbleGen 2×105K mouse whole-genome tiling arrays by Imagenes using MEF DNA from TauEGFP knock-in mice as a reference (Gene BioDesign).

Flow Cytometry

The induced efficiency of the TauEGFP-positive cells was estimated using a FACS Calibur flow cytometer (Becton Dickinson), and the flow cytometry data were analyzed using FlowJo. For intracellular flow cytometry analyses, single-cell suspensions were stained with antibodies and analyzed using a BD FACSCalibur.

Cell Transplantation and Immunohistochemistry

For TauEGFP-positive cells transplantation, adult BALB/c-nu mice (8 weeks of age) were anesthetized with 0.8% Pelltobarbitalum Natricum and received stereotaxic surgeries. About 1×105 cells in 4 μl artificial cerebrospinal fluid (aCSF) were injected into the left striatum at the following coordinates (AP=+0.5 mm, ML=−2.0 mm, DV=−3.0 mm). For immunohistochemistry on brain slices, mice were anesthetized at 4 weeks after transplantation with 0.8% pelltobarbitalum natricum and perfused with 0.9% saline solution followed by 4% ice-cold phosphate-buffered paraformaldehyde (PFA). The brains were removed and immersed in 4% PFA overnight at 4° C. Then transfer the brains sequentially into 20% and 30% sucrose to cryoprotect the tissues. After embed with OCT solution (Tissue-Tek), coronal sections were cut on a freezing microtome at a thickness of 30 μm and stored at −20° C. For immunostaining, brain sections were incubated with primary antibody overnight at 4° C. and then the corresponding secondary antibody for 2 h at room temperature. All sections were mounted by Fluoroshield with DAPI (Sigma).

Inducing Hepatocyte-Like Cells from XEN-Like Cells

1. XEN-like cells (obtained as disclosed above by culturing fibroblasts in Stage 1 cell culture medium) were seeded at a density of 50,000 cells per well of a 12-well plate (day −2).
2. On day 0 until 70% confluence, cells were switched into specification medium with DMEM medium, 1% N2, 1% B27, 1% Glutamax, 1% penicillin/streptomycin (P/S), 20 ng/ml Activin A, 20 ng/ml EGF, 20 ng/ml BMP4, long/ml FGF2 for 10 days.
3. Then cells were changed into maturation medium with modified HCM, 10 ng/ml OSM, 0.1 uM DEX for another 10 days.

Refresh the medium every day. Typical hepatocyte-like morphology emerged on about day 20. These induced hepatocyte-like cells were subjected to characterization.

Note: A relatively low initial cell density is beneficial for the hepatic induction from passaged XEN-like cells since the high proliferation rate of XEN-like cells.

Primary Hepatocytes Isolation and Culture

Mouse primary hepatocytes were isolated from mouse liver as described previously and were cultured in HCM medium (LONZA) in collagen-coated dishes for 24 hrs. for ELISA analysis. Mouse fetal liver tissue was lysed with TRI Reagent for RNA extraction.

ALBUMIN and UREA Secretion

The amount of albumin and urea in culture supernatant was measured using a mouse ALB ELISA kit or urea assay kit (from QuantiChrom™).

Results

Fine-Tuning the Chemical Recipe to Obtain XEN-Like Cells in a Robust Manner

A previously established protocol to produce chemically induced pluripotent stem cells (CiPSCs) from fibroblasts, induced XEN-like primary colonies at an early stage of reprogramming with a seven-compound cocktail (VPA, CHIR99021, 616452, Tranylcypromine, Forskolin, AM580 and EPZ004777; VC6TFAE) (Zhao et al., Cell, 163:1678-1691 (2015)) (Table 1). This study, focused on improving the yield of the Xen-like state without altering the Xen-like State. For this purpose, TD114-2 was identified as a more preferable GSK3-beta inhibitor than CHIR99021 (Table 1). By replacing CHIR99021 with TD114-2, the yield of the primary colonies was enhanced by 3 fold, without altering the establishment of the XEN-like state (FIGS. 1A and B, and data not shown). Thus, a new small-molecule cocktail was identified (VT6TFAE) to induce XEN-like cells from fibroblasts in a significantly improved manner.

Robustly Generating Neuronal-Like Cells from the XEN-Like State

A previous study identified the XEN-like state with ready-to-use characteristics of erased hallmark fibroblast genes, which can be further induced into the pluripotent state (Zhao et al., Cell, 163:1678-1691 (2015)). The present studies sought to generate other functional cells from the Xen-like cells while by-passing the pluripotent step.

Figure 1E:
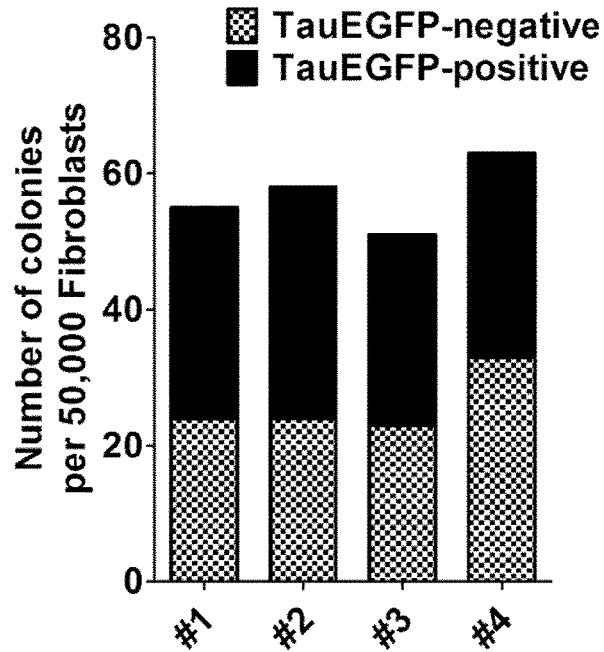
FIG. 1E shows numbers of TauEGFP-positive and -negative colonies induced from XEN-like colonies.

To induce neuronal cells from the XEN-like state, chemical compounds that facilitate neural lineage differentiation were used (FIG. 1C and Table 1). Using these chemical inducers, TauEGFP positive cells were induced as early as 4 days after neural induction indicating the acquisition of neuronal fates, with the inducing efficiency >50% after 8-12 days induction with an optimized starting cell density (FIG. 1D, data not shown and FIG. 1E). The same protocol was used to induce neuron-like characteristics from post natal fibroblasts. TauEGFP-positive cells were also generated from mature fibroblasts and the neuronal identify of the cells were confirmed by positive co-immunostaining for the neuronal markers TUJI and MAP2 (data not shown).

Figure 1F:
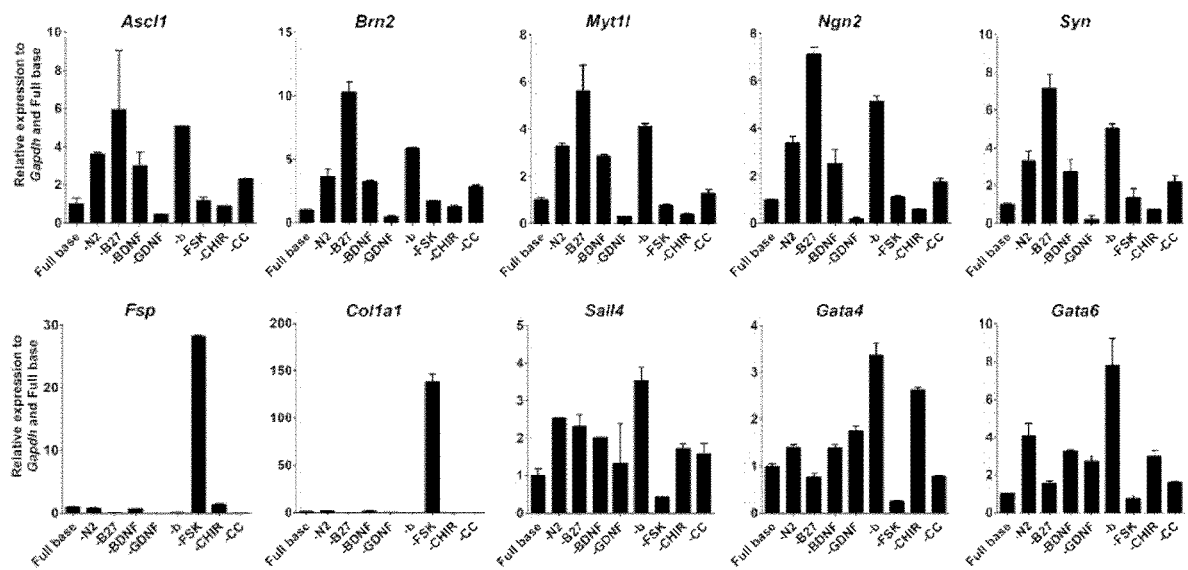
FIG. 1F shows qRT-PCR analysis of neural genes, fibroblast genes and XEN master genes regulated by components in Stage2 neural induction medium included N2, B27, BDNF, GDNF, bFGF, FSK, CHIR, Compound C (abbreviated as CC, also named as: Dorsomorphin). n=2.

The separate roles of these chemical inducers, as well as the gradients in the culture medium were further identified by examining the neural-, fibroblast- and XEN-specific genes in the absence of these factors (FIG. 1F). The data shows that the presence of GDNF and Forskolin are preferred. GDNF is important for inducing neuronal mater and functional genes, and Forskolin is important for downregulating fibroblast-specific genes.

TauEGFP positive cells could be also generated from the CHIR-induced (VC6TFAE-induced) XEN-like cells, albeit with a lower efficiency (FIG. 1D). By extending the neuronal specifying period, a number of the induced TauEGFP-positive colonies generated extensive TauEGFP-positive neurite-like branches (data not shown), indicating a maturing process. Taken together, neuronal-like cell fates could be induced from the XEN-like cells after further neuronal specification.

Induced Neuronal-Like Cells Express Neuronal Hallmark Genes

To explore the induced neuronal properties of these TauEGFP-positive cells, the expression of typical pan-neuronal markers in these cells was examined. Co-immunostaining revealed that the induced TauEGFP-positive cells with extensive neurite growth co-expressed multiple neu- The Expression Profile of the Induced Neurons Resembles that of Primary Neurons To better understand the properties of the induced cells, RNAseq was performed to analyze the expression pattern of the induced neurons. Hierarchical clustering analysis revealed that the induced neurons grouped closely with the primary neurons and distinguished from fibroblasts (data not shown). Further analysis revealed that after chemical induction, the induced cells showed enriched expression of multiple neuronal-specific genes, including pan-neuronal genes (Mapt, Map2 and Dcx) and functional synaptic components (Stmn3, Stmn4 and Sypl), whereas the expression of fibroblast-hallmark genes was significantly downregulated (data not shown).

Figure 2A:
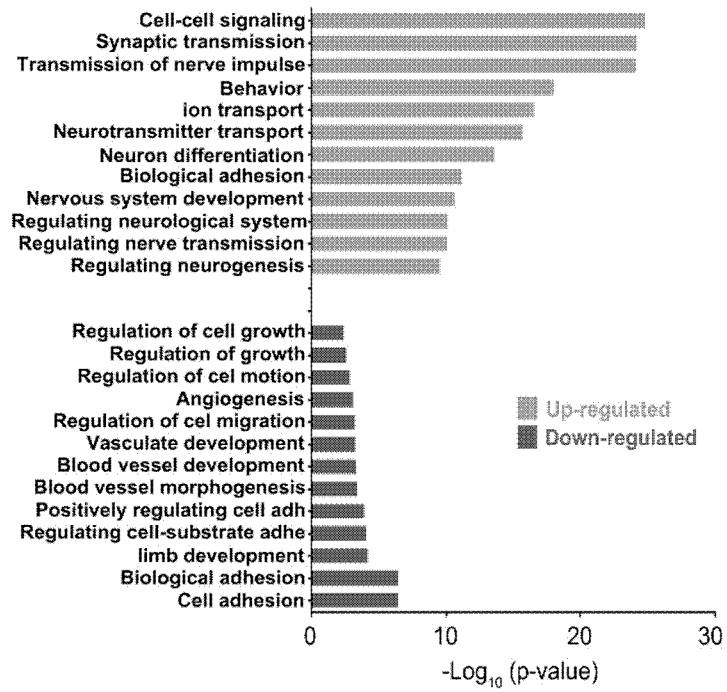
FIG. 2A shows GO analysis for genes that were most robustly upregulated or downregulated by chemical induction (>10-fold differentially expressed)

To further understand the chemical reprogramming process, the genes that were most robustly upregulated or downregulated by chemical induction (>10-fold differentially expressed) were selected for GO (gene ontology) analysis. The results revealed that the upregulated genes were highly enriched in synaptic transmission, ion transport, neuron differentiation and neuron development, crucial biological processes implicated in neurogenesis (FIG. 2A), whereas the downregulated genes were involved in cell adhesion, cell migration and cell growth (FIG. 2A). Together, these results demonstrate that these chemically induced neurons have a transcriptional profile resembling that of primary neurons and distinct from that of the original fibroblasts.

Functional Properties and Maturation of the Induced Neurons

Figure 2B:
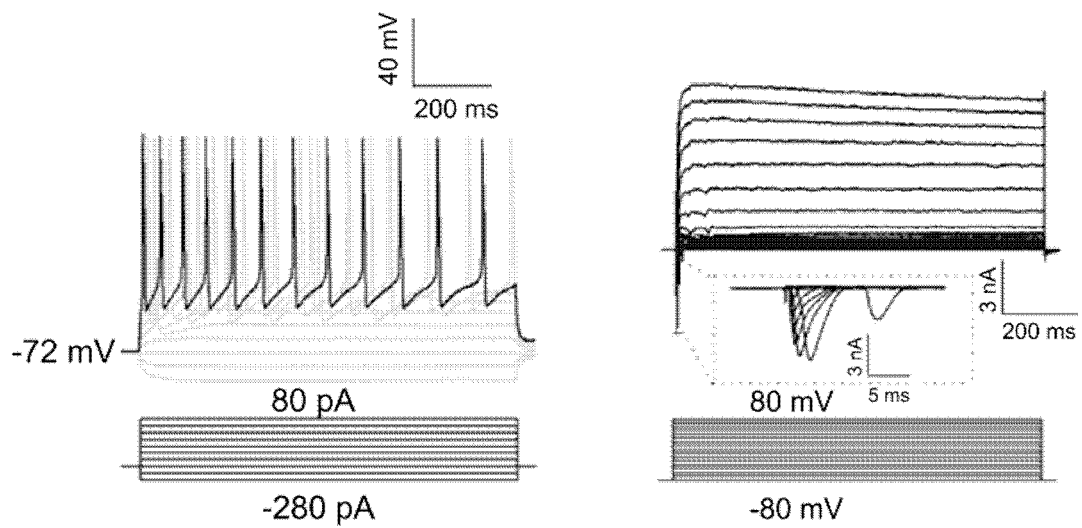
FIG. 2B shows electrophysiological functional properties of the induced TauEGFP-positive cells without co-culturing with astrocytes. n=3. The data are presented as the mean+/−SEM.
Figure 2C:
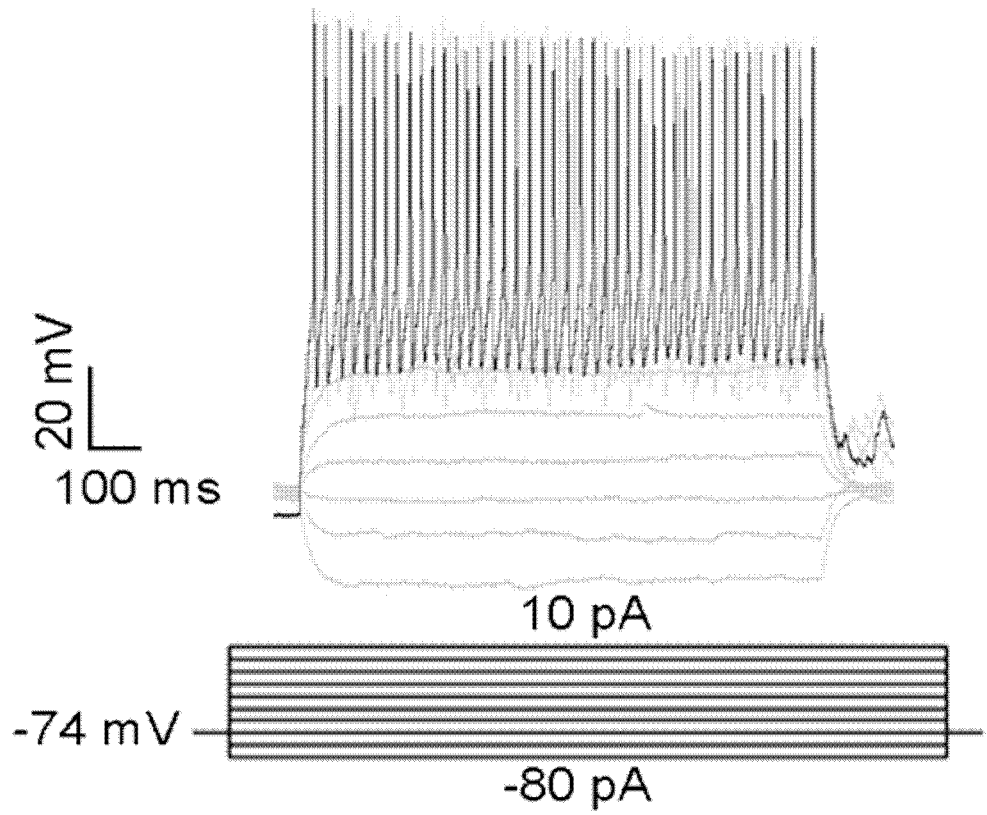
FIG. 2C shows action potentials were elicited on TauEGFP-positive induced cells. One exemplary trace of action potential was highlighted. n=11.
Figure 2D:
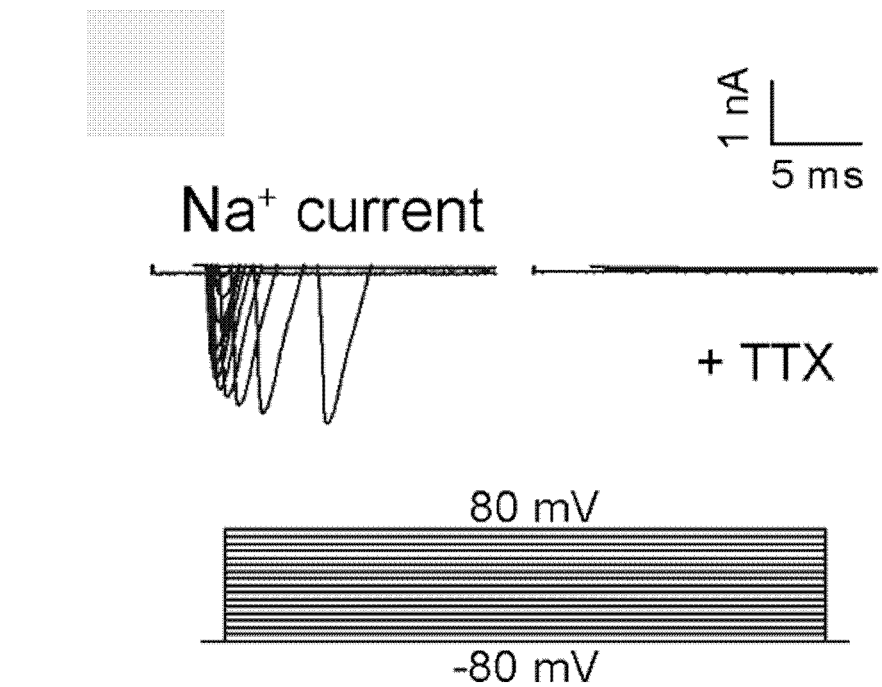
FIG. 2D shows whole-cell voltage-clamp recording of TauEGFP-positive cells and inward currents were recorded, and the sodium currents were blocked by tetrodotoxin (TTX). n=11.

To examine the electrophysiological functional properties of the induced neurons, whole-cell patch-clamp recordings were preformed. By depolarizing the membrane in current-clamp mode, action potentials (APs) were elicited on the induced TauEGFP-positive neurons after the 12+12 days' chemical induction (FIG. 2B and Table 3).

TABLE 3

Electrophysiological properties of the chemically-induced neurons from embryonic fibroblasts (MEFs)

| Induction | Rm (MO) | Cm (pF) | RMP (mV) | Threshold (mV) | Apamp (mV) | Ina-Max (pA) | N |
|---|---|---|---|---|---|---|---|
|   | 627.57 ± 77.55 | 28.59 ± 9.14 | −32.40 ± 2.57 | 29.59 ± 1.97 | 74.17 ± 3.24 | −2884.47 ± 311.01 | 11/13 |
| * | 594.70 | 12.03 | −39.81 | −41.09 | 74.44 | −2397.54 | 1/13* |
| * | 695.40 | 20.14 | −32.67 | −37.50 | 66.79 | −3840.30 | 1/13* |
|   | 415.40 | 40.50 | −35.83 | −30.47 | 84.60 | −2965.02 | 1/13 |
|   | 512.50 | 27.64 | −36.68 | −17.23 | 70.01 | −2940.01 | 1/13 |
|   | 924.10 | 26.69 | −31.30 | −29.77 | 78.22 | −2141.63 | 1/13 |
|   | 648.90 | 11.02 | −23.66 | −24.69 | 60.47 | −1621.15 | 1/13 |
|   | 1157.00 | 6.05 | −23.55 | −29.18 | 79.93 | −1928.12 | 1/13 |
|   | 210.00 | 17.81 | −15.83 | −22.99 | 59.28 | −2381.39 | 1/13 |
|   | 403.90 | 25.12 | −37.05 | −32.41 | 74.62 | −3241.35 | 1/13 |
| 0 | 691.70 | 12.27 | −33.90 | −29.02 | 70.89 | −2931.56 | 1/13 |
| 1 | 649.70 | 115.16 | −46.10 | −31.13 | 96.65 | −5341.09 | 1/13 |

* without co-culturing with astrocytes.
Rm: input resistance; Cm: membrane capacitance; RMP: resting membrane potential; APthreshold: action potential threshold; APamp: action potential amplitude; Ina-max: maximum amplitude of sodium current.
All the data are mean +/− SEM.

ronal-specific proteins, including TUJ1, MAP2, NF—H and surrounding synapsin-positive puncta (data not shown). Furthermore, both excitatory glutamatergic neurons and inhibitory GABAergic neurons were generated after an extended neuronal specifying period for about 18 days, as detected by the co-expression of vGLUT1 (80% efficiency) and the co-expression of GABA (5% efficiency) i.e., 80% vGLutl/TauEGFP double positive and 5% GABA/TauEGFP positive cells were obtained (data not shown). Examination of the induced cell population also revealed about 20% GFAP positive astrocyte-like cells (data not shown).

Figure 2E:
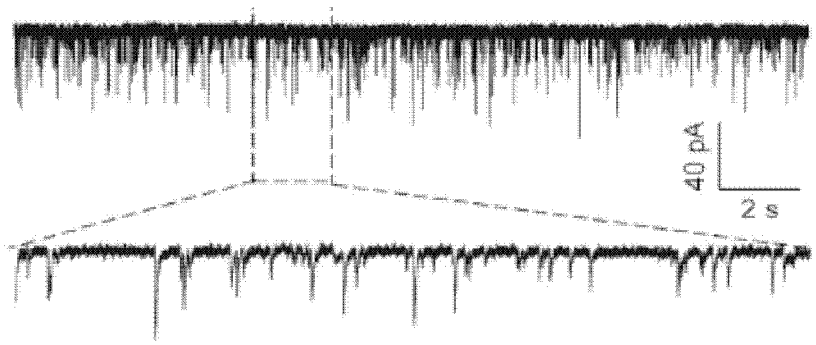
FIG. 2E shows spontaneous excitatory postsynaptic currents (EPSCs) were recorded after co-culturing with primary astrocytes, which were blocked with 20 μM CNQX plus 50 μM AP5. n=6.
Figure 2F:
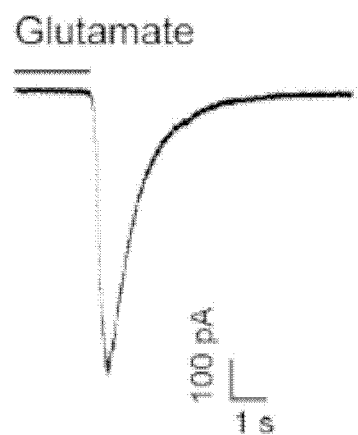
FIG. 2F shows focal application of 100 μM Glutamate induced inward membrane currents. n=5.

In addition, in the voltage-clamp mode, fast, inactivating inward and outward currents were also recorded on the induced neurons, corresponding to the opening of voltage-dependent K+- and Na+-channels of these cells (FIG. 2B and Table 3). These results reveal that functional neurons can be induced by using this XEN-like state based chemical reprogramming. To further enhance functional maturity, the induced neuronal-like cells were re-plated onto a pre-existing monolayer culture of primary astrocytes, as previously reported (Li et al., *Cell Stem Cell,* 17:195-203 (2015)). After re-plating, the induced TauEGFP-positive cells showed more complex neuronal morphologies, indicating a maturing process (data not shown). The functional membrane properties of the induced cells were further improved (85%, n=13 i.e., 85% of the examined cells were functional) (data not shown, 2C and 2D; Table 3) and spontaneous excitatory postsynaptic currents (EPSCs) were recorded on the induced TauEGFP-positive cells (54.5%, n=11), which could be blocked by the specific receptor antagonists 6-cyano-1007-nitroquinoxaline-2,3-dione (CNQX) and 2-amino-5-phosphonovaleric acid (AP5) (FIG. 2E). In addition, the mature neuronal transcriptional factor, NEUN, was also detected in up to 80% of the induced TauEGFP-positive cells (data not shown). Functional subtype properties of the induced neurons were confirmed by the induction of inward membrane currents by focal application of 100 μM Glutamate (FIG. 2F). These results reveal that the induced neurons show functional mature properties and are capable of forming functional synapses after further maturation. Like naturally occurring neurons, the chemically induced neurons in these studies do not depend on BDNF or GDNF for survival. To demonstrate this, BDNF and/or GDFN were withdrawn from the culture medium for the induced neurons.

The results revealed that the CiLR neuronal survival is not dependent on BDNF or GDNF, which is similar for culturing primary neurons. No obvious cell death or neuronal degeneration after withdrawing BDNF and/or GDFN from the culture medium (data not shown).

Generating XEN-Like Cells-Derived Neurons from Newborn and Adult Fibroblasts

Figure 2G:
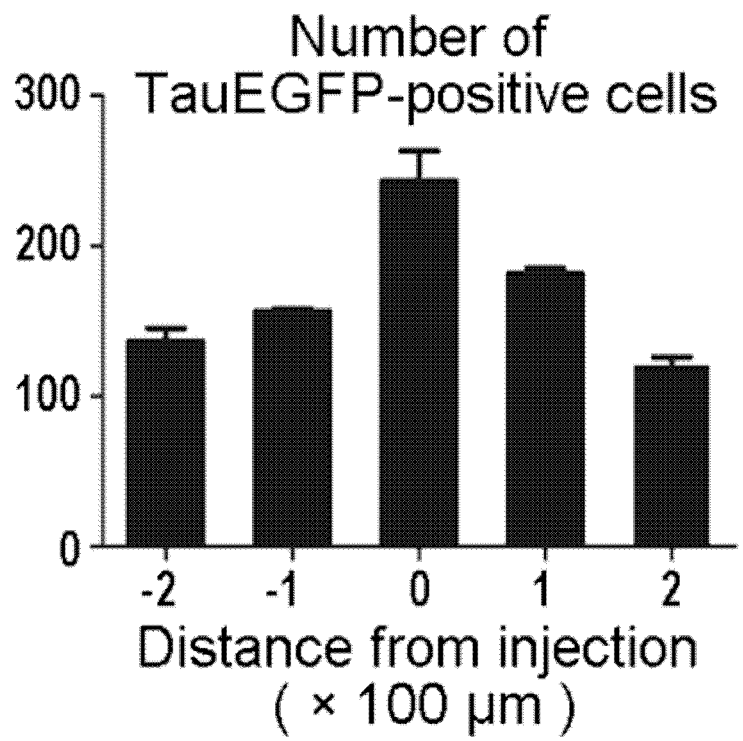
FIG. 2G is a bar graph showing quantification of TauEGFP-positive cells at different distances from the injected site. n=2.
Figure 2H:
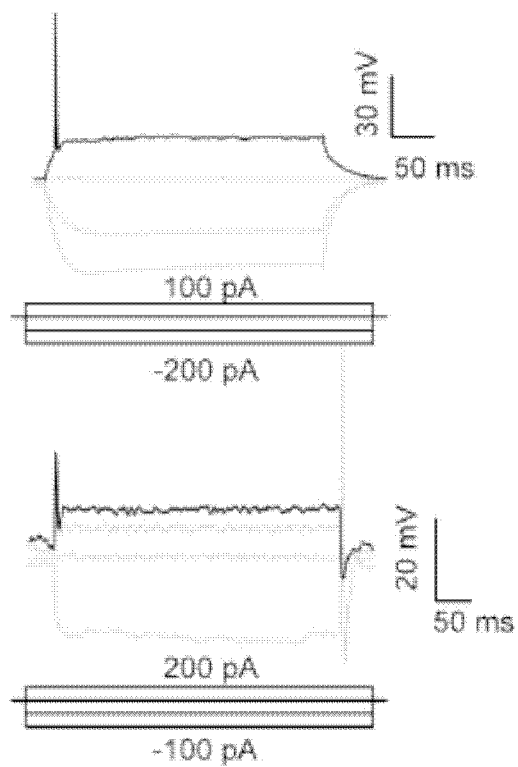
FIG. 2H shows action potentials were elicited on TauEGFP-positive cells after being transplanted into brain striatum (28 days and 35 days). One exemplary trace of action potential was highlighted. n=7.
Figure 2I:
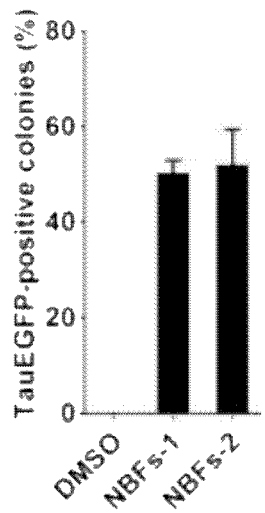
FIG. 2I shows generation of CEN-like cells-derived neurons from mouse newborn fibroblasts (NBF).
Figure 2J:
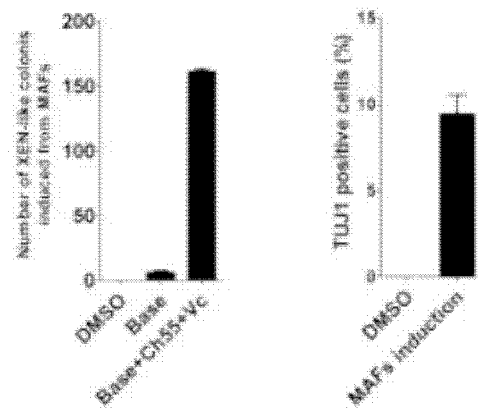
FIG. 2J shows generation of CEN-like cells-derived neurons from mouse adult fibroblasts (MAF).

To demonstrate the applicability of the disclosed methods, the methods were used to reprogramming newborn and adult fibroblasts. By using the same protocol of inducing embryonic fibroblasts (discussed herein), XEN-like derived neurons could be efficiently generated from newborn fibroblasts (postnatal day 3) (FIG. 2I). For reprogramming adult fibroblasts derived from >8 week old mice, the XEN-like cells could be induced, albeit with a lower efficiency (FIG. 2J), which may result from the cell senescence during culturing. By providing two additional small-molecule compounds, vitamin C (to suppress cell senescence and enhance cell proliferation) and CH55 (to enhance reprogramming efficiency) the efficiency of generating XEN-like cells were significantly improved in 12 days' induction and neuronal cells were also generated from these XEN-like cells following 12 days' neuronal specification (FIG. 2J and FIG. 1C). These results reveal that the methods disclosed herein methods can also be applied for reprogramming postnatal fibroblasts.

Induced Neurons Survive and Mature after Transplantation into Adult Mouse Brain

To examine the in vivo functional competency of the XEN-like state-derived chemically-induced neurons, the resulting TauEGFP-positive neuronal cells were transplanted into the striatum of adult mice (>8 weeks old). After 4 weeks of transplantation, surviving TauEGFP-positive cell grafts were clearly detected at the injected sites (data not shown). The neuronal identity and maturing properties of the cell transplants were further confirmed by co-immunostaining for neuronal-specific genes, including the mature neuronal transcriptional factor NEUN, TUJI and MAP2 (data not shown, FIG. 2G). Furthermore, the grafting TauEGFP-positive cells in fresh brain slice showed functionally electrophysiological properties (FIG. 2H). Taken together, these results indicate the in vivo functionality of these XEN-like state derived neuronal cells.

Lineage Tracing Confirms the Fibroblast Origins of the Induced Neurons

Figure 3A:
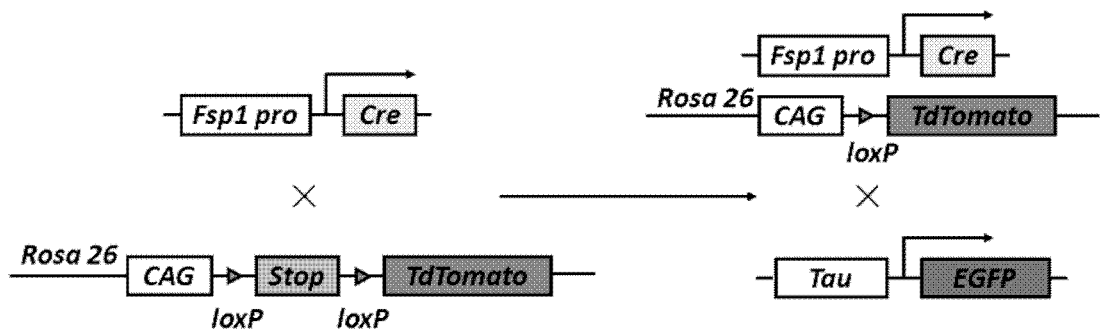
FIG. 3A is a scheme of lineage tracing system.

To examine the fibroblast origin of the induced neurons, original fibroblasts expressing fibroblast specific protein 1 (Fsp1) were traced by using the Cre-LoxP system, as previously reported (*Cell Stem Cell*, 17:195-203 (2015)) (FIG. 3A). These studies sought to demonstrate that the induced neurons obtained herein where originally derived from fibroblasts, rather than neuronal progenitor cells that can contaminate MEF during preparation.

Figure 3B:
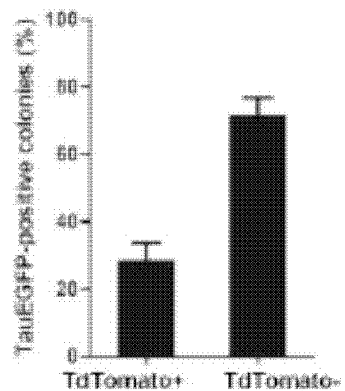
FIG. 3B shows quantification of TauEGFP-positive colonies induced from TdTomato-positive and -negative cells. The induced TdTomato-positive cells induced from XEN-like cells expressed pan-neuronal markers TUJ1, NF—H and SYN.
Figure 3C:
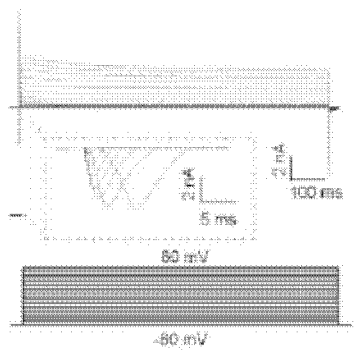
FIG. 3C shows whole-cell voltage-clamp recording of TdTomato-positive cells induced from XEN-like cells and inward and outward currents were recorded. n=4.

The initial fibroblasts were not all tdTomato-positive, after chemical induction, approximately 30% of the induced tdTomato-positive colonies were TauEGFP-positive (Figure data not shown and FIG. 3B). Co-immunostaining revealed that the induced TauEGFP and tdTomato double positive cells with extensive neurite growth co-expressed multiple neuronal-specific proteins with tdTomato, including TUJ1, NF—H and SYN (data not shown). Furthermore, these TauEGFP and tdTomato double positive cells could also develop into functional neurons after further neuronal specification. Patch-clamp recordings revealed functional properties of the induced TauEGFP and tdTomato double positive neurons (data not shown and FIG. 3C). These results provide direct genetic proof that functional neurons can be induced from the fibroblast origins by using this chemical induction strategy.

Figure 3D:
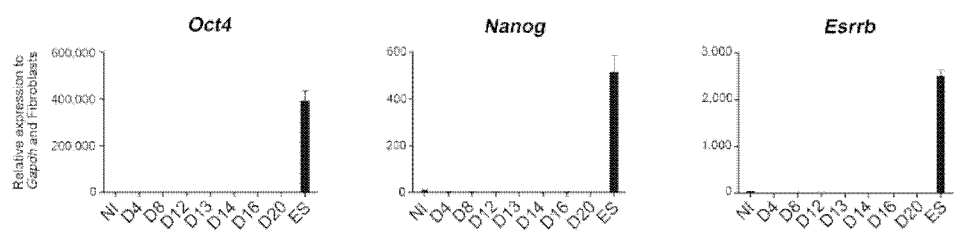
FIG. 3D shows RT-qPCR analysis for hallmark pluripotent genes (Nanog, Oct4 and Esrrb) through the chemical induction process. n=2.

Lineage Tracing Confirms that Chemical Reprogramming Bypasses Acquisition of Pluripotency To further investigate the reprogramming process and determine whether the chemical induction bypasses the pluripotent state, real-time qPCR and immunostaining was performed at different induction phases. Endogenous expression of the hallmark pluripotent genes, including Oct4, Nanog and Esrrb, was not detected throughout the chemical reprogramming process (FIG. 3D).

To carefully investigate the possibility of inducing neural differentiation from a transient acquisition of pluripotent state, the endogenous expression of Oct4, the core transcription factor governing pluripotency, was traced by using the CreER-LoxP system, as previously reported (Bar-Nur et al., *Nat Biotechnol.*, 33:761-768 (2015)). By introducing the four Yamanaka transcriptional factors, tdTomato-positive iPS colonies were efficiently induced from fibroblasts within 10 days (data not shown), which confirmed the reliability of this lineage tracing system. In contrast, no tdTomato-positive colonies were detected after chemical induction, even after establishing neuronal fate (data not shown and FIG. 3E). Together, these results show that this XEN-like state based chemical reprogramming approach to generate neurons indeed bypasses the acquisition of pluripotency.

Embryo-Derived XEN Cells Resemble the Chemically-Induced XEN-Like Cells for Neuronal Induction To further understand the XEN-like state based neural lineage reprogramming and examine the established method, chemically derived eXEN cell lines (CeXENs; embryo-derived XEN cells (eXEN) were prepared from blastocysts as previously reported (Zhao et al., *Cell*, 163: 1678-1691 (2015)). These CeXENs expressed the key transcriptional factors governing the XEN state, GATA4, SALL4, SOX17 and GATA6 (data not shown). CeXENs were induced into neuron-like cells using the stage 2 cocktail disclosed herein without overexpressing Sox2 (data not shown). This was accomplished by extending the neuronal induction stage from 12 to 24 days and modifying the concentration of forskolin at this stage (50 uM FSK to establish the CeXEN line and 10 uM for inducing into neurons).

These results reveal that the blastocysts-derived XEN-like cells could also be induced into neuronal cells following the protocols disclosed herein.

Figure 4A:
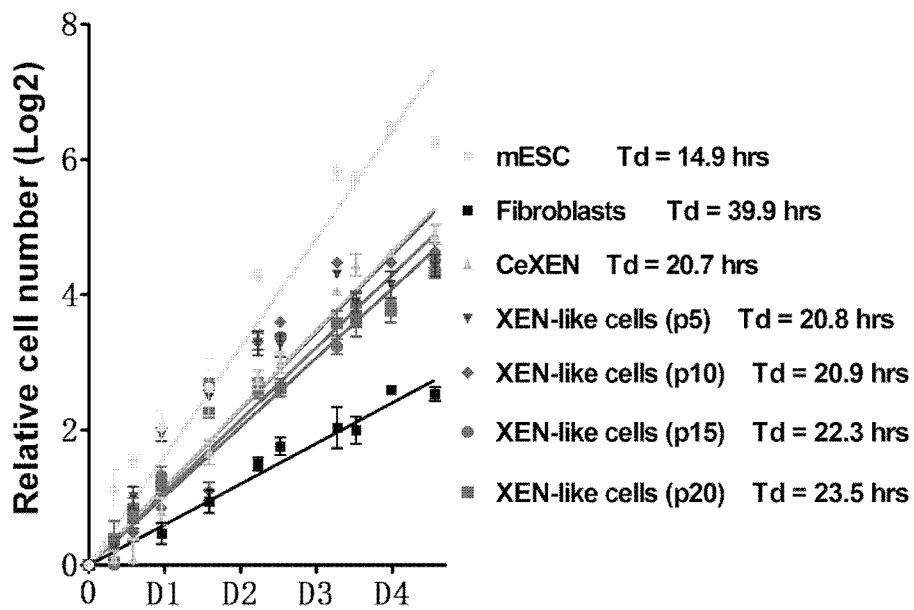
FIG. 4A shows doubling time analysis of induced XEN-like cells (different passages), ESCs and fibroblasts. n=3.
Figure 4D:
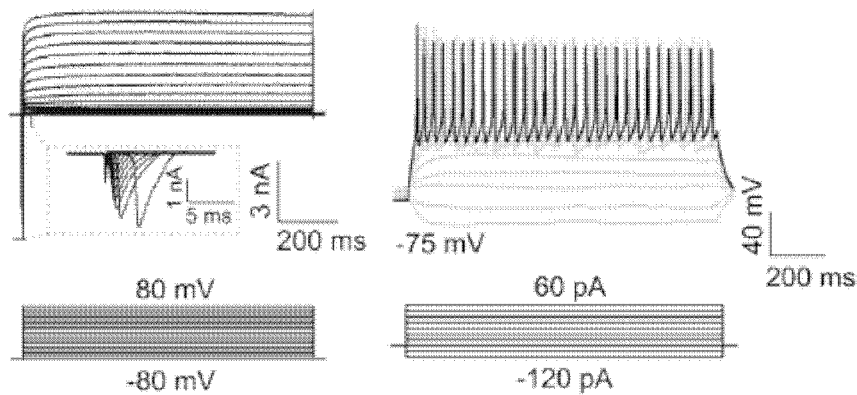
FIG. 4D shows induced TauEGFP-positive neurons from long-term expanded XEN-like cells (after 20 passages) show electrophysiological functional properties. n=12.

Long-Term Expanding Chemically-Induced XEN-Like Cells Retaining Genome Stability and Neuronal Specifying Potentials To further explore the characteristics of the XEN-like state, the growth rate of the chemically-induced XEN-like cells was investigated by evaluating the doubling time. The induced XEN-like cells grew much faster (about 20 hours for doubling) than original fibroblasts (about 40 hours for doubling), which was comparable to CeXEN cells and slower than ESCs (about 15 hours for doubling) (FIG. 4A). In recognition of the highly proliferative property of the chemically-induced XEN-like cells, we further explore the expandability of these XEN-like intermediates. By using the TD114-2 based culture condition, the XEN-like colonies could be expanded long term (at least 20 passages tested), even in a single-colony selecting and single-cell digesting manner, at average ratio of 1:20-30 every 3-4 days (data not shown). Despite the highly expandable properties, no tumorigenesis was detected after injecting the XEN-like cells into the immunodeficient (SCID) mice (XEN-like cells at passage 6 and passage 19 tested) (data not shown). In addition, as revealed by results of karyotype and comparative genomic hybridization (CGH) analysis, the long-term expanded XEN-like intermediates retained the genetic integrity and genome stability (FIG. 4B-C). Most importantly, besides retaining the XEN-like featured expression patterns, as revealed by the results of co-immunostaining and electrophysiological functional assay, these expanded XEN-like cells retained the neuronal specifying potentials, without compromising the neuronal inducing efficiency even after 20 passages, and the resulting neurons from the long-term passaged XEN-like cells shown functional mature properties (data not shown and FIG. 4D-F; Table 4).

Dynamic Transcriptional Changes Underlying the XEN-Like Based Chemical Lineage Reprogramming To understand the lineage plasticity of XEN-like cells, RNA-seq analysis for single-colony derived XEN-like cell lines was preformed. The results revealed that the fibroblast-specific transcriptional program was dramatically erased during the stage 1 XEN-like induction (data not shown). Furthermore, the results revealed a unique transcriptional character underlying XEN-like state for co-expressing master genes governing cell fates towards three germ layers (data not shown), suggesting the potential lineage plasticity of the XEN-like intermediates.

Figure 5A:
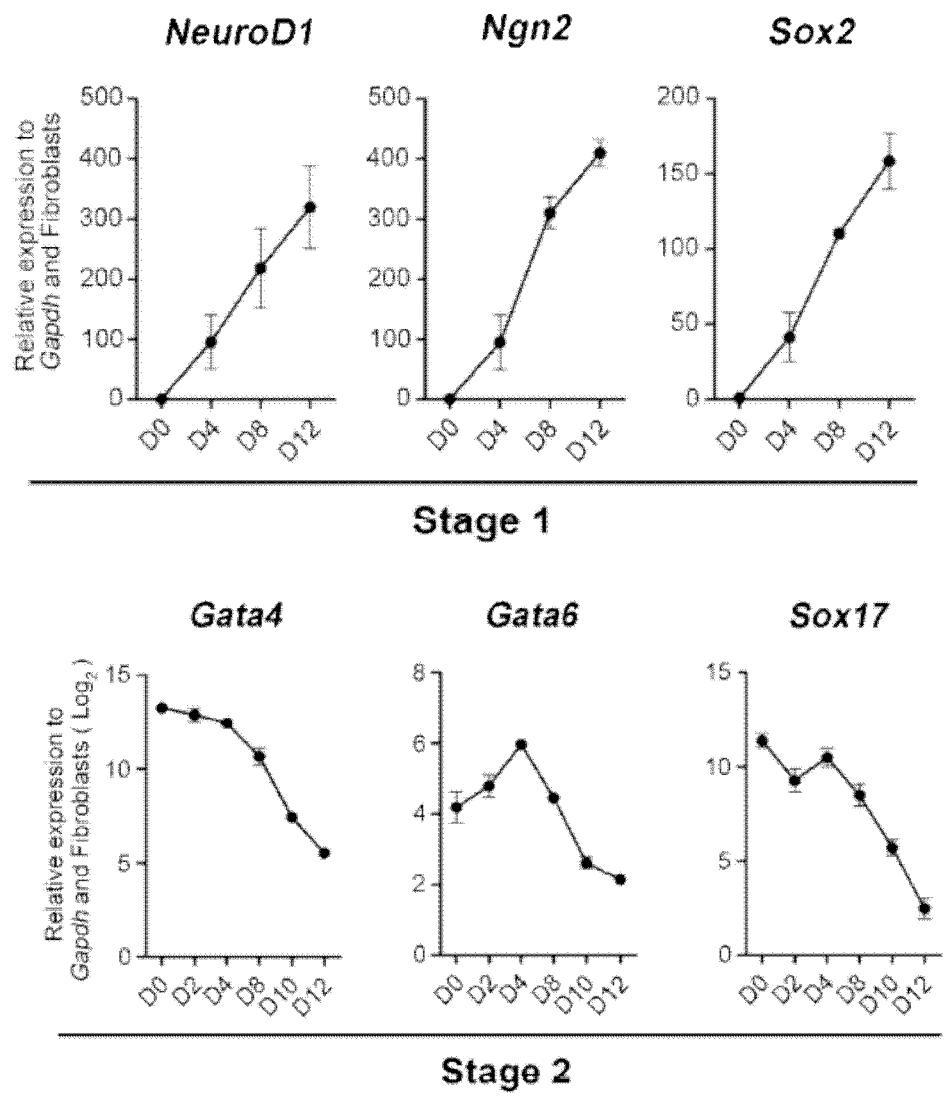
FIG. 5A shows induced expression of neural-mastering genes (NeuroD1, Ngn2 and Sox2) during stage 1 chemical induction, and decreasing expression of XEN-mastering genes (Gata4, Gata6 and Sox17) at stage 2. n=2.

To investigate the mechanism of the featured XEN-like state based lineage reprogramming, transcriptional changes of the identified master genes governing distinct cell fates were examined by RT-qPCR analysis. Besides the transcriptional downregulation of fibroblast-specific program consistent with the results from the single-colony perspective, neuroectoderm-specific (SOX2, Ngn2 and NeuroD1) and the XEN-master genes (GATA6, Sox17, Sall4, Gata4) were both upregulated during the first-stage chemical induction towards the XEN-like state (FIG. 5A and data not shown). Starting from the later-stage neuronal specification at day 12 (FIG. 1C), the XEN master genes were robustly downregulated (FIG. 5A; (Stage 2)).

Figure 5B:
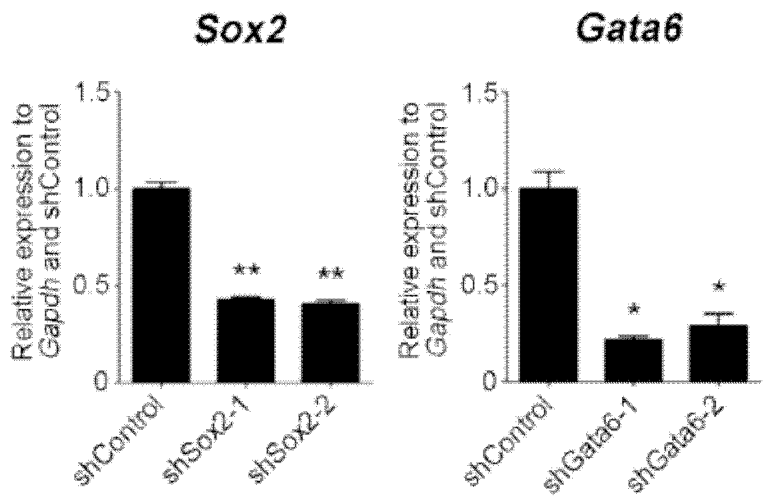
FIG. 5B shows the expression of Sox2 or Gata6 after shRNA knockdown. shControl: Non-targeting vector shRNA. n=2.
Figure 5C:
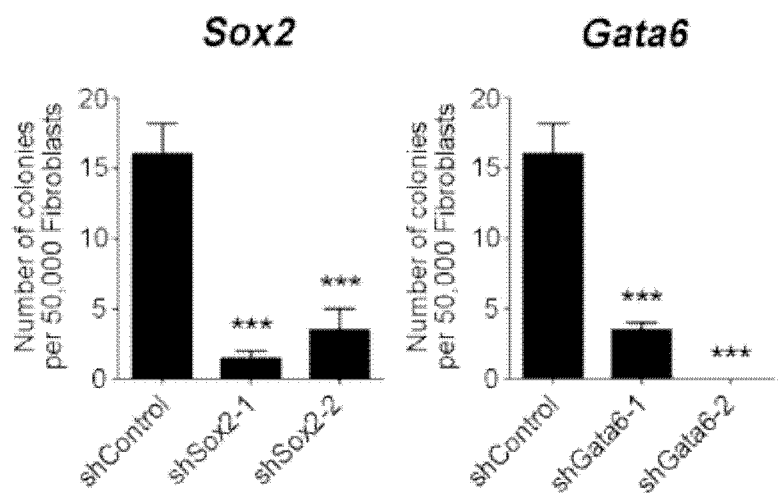
FIG. 5C shows inducing efficiency of primary XEN-like colonies and TauEGFP-positive colonies by knocking down neural-master gene (Sox2) or XEN-master gene (Gata6). n=2.
Figure 5C:
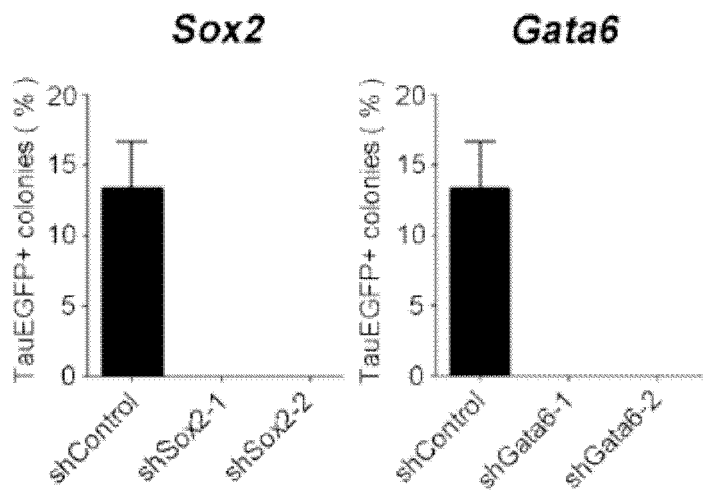

To further examine and confirm the roles of the neural and XEN mastering genes in this featured lineage reprogramming, a knockdown these genes (Sox2 and Gata6) was performed during the reprogramming process, which suppressed the generation of XEN-like colonies and blocked the neuronal induction (FIGS. 5B and 5C), demonstrating the essential roles of these endogenous mastering genes for the chemical reprogramming. Taking together, these results suggest dynamic transcriptional changes during the chemical reprogramming and reveal the essential factors for the XEN-like state based lineage reprograming.

Hepatocyte-Like Cells were Generated from the XEN-Like Cells

In the next set of studies XEN-like cells into hepatic cells of endoderm by modifying the culture medium to favor hepatic cell fate specification (Cai, et al., *Hepatology*, 45:1229-1239 (2007); Song, et al., *Cell Res.*, 19:1233-1242 (2009)). Typical hepatocyte morphology emerged after the 20-day induction, even when induced from long-term expanded XEN-like cells (>passage 20) (data now shown).

Figure 5D:
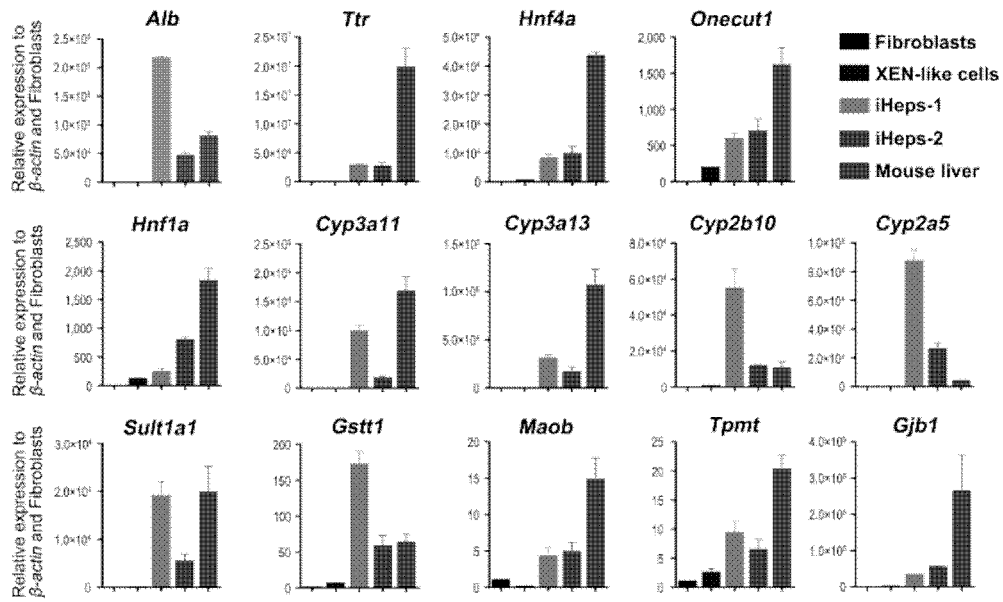
FIG. 5D shows qRT-PCR analysis of hepatic hallmark genes in fibroblasts, XEN-like cells, induced hepatocyte-like cells from XEN-like cells (from two batches of experiments) and primary hepatocytes (isolated from 2-day postnatal mouse). n=3.

RT-qPCR analysis was performed to examine the hepatic-specific gene expressions. The XEN-like induced hepatocyte-like cells co-expressed hepatic specific genes, including Alb, Hnf4α, Hnf1a and Ttr (FIG. 5D and Table 2). Furthermore, the induced hepatocyte-like cells also expressed cytochrome P450 enzymes (CYPs), as key functional hepatic genes (FIG. 5D and Table 2). The induced expression of hepatic hallmark genes, a-fetoprotein (AFP) and albumin (ALB), were further confirmed by co-immunos-

TABLE 4

Electrophysiological properties of the chemically-induced neurons from passage 20 XEN-like cells

| Induction | Rm (MO) | Cm (pF) | RMP (mV) | Threshold (mV) | Apamp (mV) | Ina-Max (pA) | N |
|---|---|---|---|---|---|---|---|
|  | 501.68 ± 157.78 | 25.52 ± 3.77 | −25.17 ± 2.25 | −29.44 ± 2.45 | 74.68 ± 3.56 | −3421.28 ± 601.13 | 12/13 |
| 1* | 338.50 | 9.26 | −15.96 | −29.79 | 50.44 | −1415.14 | 1/13 |
| 2* | 2025.00 | 16.80 | −27.77 | −21.06 | 76.28 | −2535.19 | 1/13 |
| 3 | 367.10 | 16.87 | −14.25 | −51.57 | 51.39 | −1502.67 | 1/13 |
| 4 | 113.60 | 22.48 | −29.50 | −36.26 | 88.17 | −6842.51 | 1/13 |
| 5 | 265.60 | 19.48 | −24.02 | −29.48 | 80.12 | −1832.77 | 1/13 |
| 6 | 721.40 | 11.28 | −22.62 | −35.25 | 73.62 | −1083.47 | 1/13 |
| 7 | 258.60 | 23.03 | −16.36 | −22.55 | 75.40 | −5413.31 | 1/13 |
| 8 | 1020.00 | 41.30 | −28.06 | −25.81 | 83.96 | −3185.71 | 1/13 |
| 9 | 151.20 | 44.04 | −37.95 | −23.21 | 79.84 | −5265.45 | 1/13 |
| 10 | 224.30 | 50.26 | −30.27 | −24.25 | 71.92 | −3429.55 | 1/13 |
| 11 | 388.00 | 24.74 | −19.15 | −24.25 | 76.07 | −1969.07 | 1/13 |
| 12 | 146.90 | 26.70 | −36.11 | −29.8141 | 89.00 | −6580.56 | 1/13 |

Figure 5E:
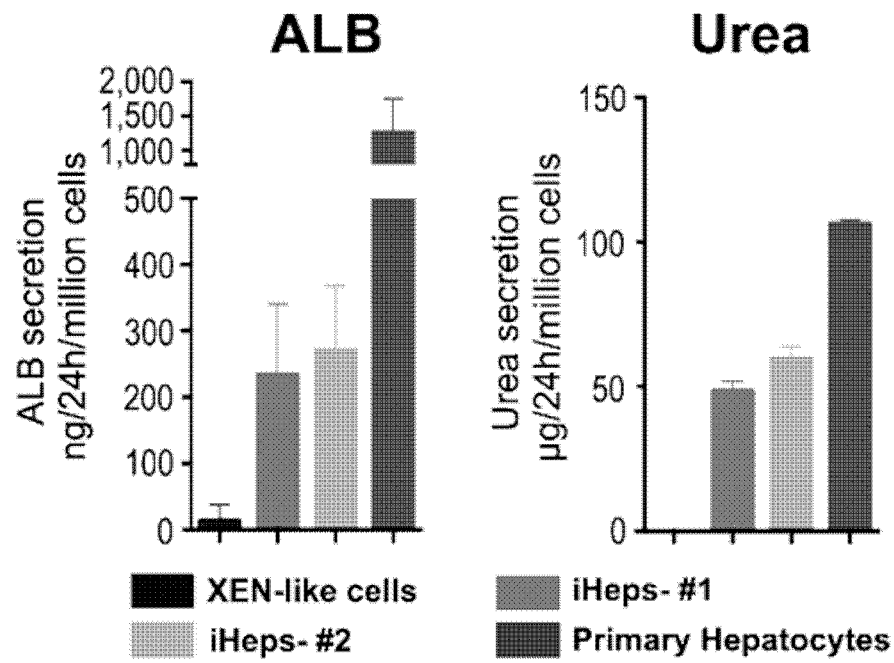
FIG. 5E shows quantitative analysis of ALBUMIN and Urea secretion among XEN-like cells, iHeps (chemically induced hepatocytes) from XEN-like cells (>passage 20) and primary hepatocytes by ELISA. n=3. The data are presented as the mean+/−SEM. *P<0.05; P<0.01; *P<0.001 (Student's t-test).
Figure 5F:
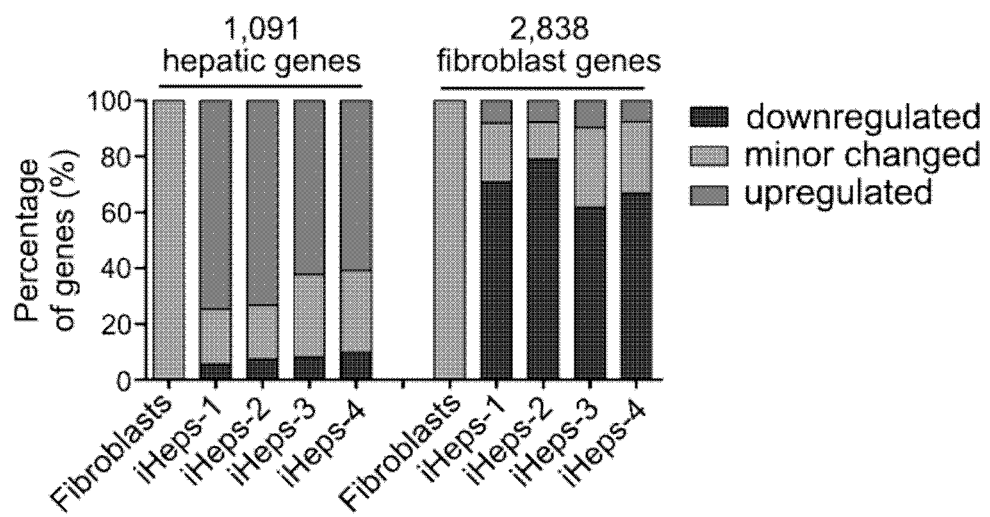
FIG. 5F shows Number of genes that are upregulated or downregulated during the XEN-to-hepatocytes conversion process. "Upregulated" represents genes whose expression level was upregulated by more than 2-fold compared to fibroblasts, while "downregulated" represents genes whose expression level was downregulated by more than 2-fold compared to fibroblasts.

*without co-culturing with astrocytes.
Rm: input resistance; Cm: membrane capacitance; RMP: resting membrane potential; APthreshold: action potential threshold; APamp: action potential amplitude; Ina-max: maximum amplitude of sodium current.
All the data are mean +/− SEM.

taining (data now shown), with the induced efficiency >20%. RNAseq results revealed that the global gene expression of the XEN-derived hepatocytes grouped closely to the primary hepatocytes and distinguished from fibroblasts. The results also revealed that the endogenous hepatocyte-fate-specific program were significantly upregulated while the endogenous fibroblast-fate-specific program were significantly downregulated after chemical induction (FIG. 5F).

To explore the functional properties of XEN-like induced hepatocyte-like cells, albumin and urea secretion by the induced hepatocyte-like cells was examined. The results revealed that the induced hepatocyte-like cells were able to efficiently secret albumin and urea (FIG. 5E). Taking together, these results demonstrate that hepatocyte-like cells could also be induced from XEN-like cells.

Discussion

In this study, an efficient system to induce XEN-like cells from fibroblasts by using only chemical compounds was developed. This was used to provide a new lineage reprogramming route to generate functional neurons and hepatocyte-like cells from somatic fibroblasts via a featured intermediate XEN-like state, bypassing the pluripotent stage. Furthermore, a robust method for long-term expansion of the induced XEN-like cells (at least 20 passages), retaining the genome stability and lineage specifying competency was established. In addition, featured transcriptional changes during the XEN-like state based lineage reprogramming were identified. By further specifying from the intermediate XEN-like state with erased original somatic transcriptional program, these chemically-induced XEN-like cells could be developed into specific lineages, even specified subtype cells.

Figure 3E:
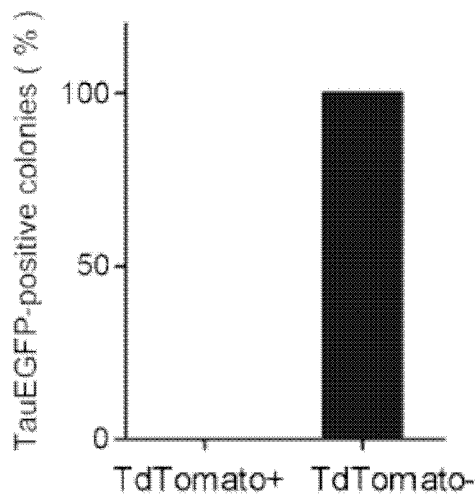
FIG. 3E shows percentage of TauEGFP-positive colonies induced from the TdTomato labelled fibroblasts.

One important finding is that the chemically-induced XEN-like state is not restricted to be reprogrammed to pluripotency but amenable to be induced into functional specified cells such as neurons and hepatocytes. As revealed by the results of electrophysiological functional assays, XEN-like cell-derived neurons could be elicited to fire action potentials, with a significantly improved efficiency when compared to previous reports (Li et al., *Cell Stem Cell*, 17:195-203 (2015)). Furthermore, the induced neurons formed functional synapses in culture dish with co-cultured primary neurons, even after long term passages (FIGS. 2C-2H and 4A-E). More importantly, after being transplanted into brains of adult mice, these cells survived and further matured, expressing functional mature neuronal genes, and developed functional properties. In addition, lineage tracing showed that the induction of neuronal cells via the XEN-like state bypassed the acquisition of the pluripotent stage (FIG. 3E and data not shown). Collectively, these data demonstrate that functional specified cells could be induced from the chemically induced XEN-like cells bypassing the pluripotent stage. Intriguingly, the XEN-like state is accessible not only to neuronal fate but also to other lineages. The induced XEN-like cells expressed master genes governing cell fate choices towards different germ layers and cell lineages, and the upregulation of neuroectoderm- and mesendoderm-specific master genes was observed during the first-stage chemical induction (FIG. 5A), suggesting more broad lineage plasticity from the induced XEN-like state, besides being specified into neuronal cell fate. In support of this notion, by employing an induction condition favoring liver fate, hepatocyte-like cells could be induced from the XEN-like cells (FIGS. 5D and 5E). These induced hepatocyte-like cells showed the upregulation of hepatic marker genes (FIG. 5D) and exhibited hepatic functional features including albumin and urea secretion (FIG. 5E). The induction of neuronal and hepatocyte-like cells from the XEN-like cells indicates that other cell lineages can be obtained via the XEN-like state.

Figure 4E:
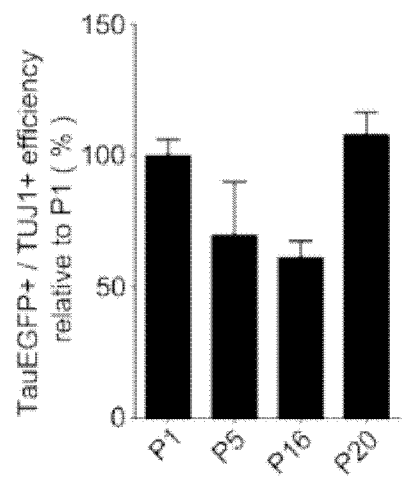
FIG. 4E shows quantification of inducing efficiency of TauEGFP-positive cells from XEN-like cells at different passages (the inducing efficiency from XEN-like cells at passage 1 was set as 100%). n=2.
Figure 4F:
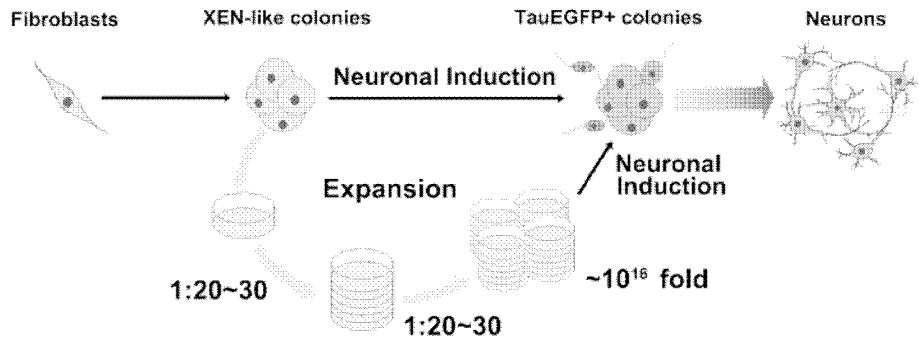
FIG. 4F is a schematic diagram of scalable XEN-like state based chemical reprogramming. The data are presented as the mean+/−SEM.

Notably, the expandability of the induced XEN-like cells confers a scalable cell resource for generating desirable cells. As revealed by the doubling time assay in this study, the XEN-like cells proliferated robustly, without compromising the neuronal induction efficiency after passages (FIG. 4A and FIG. 4E). Under the disclosed XEN-like culture condition, at least ~1016 neuronal cells could be obtained from a single fibroblast within 80 days: a single fibroblast could be induced into a single XEN-like colony comprising about 1,000-3,000 cells within 12 days, expanded for 20 passages at average ratio of 1:20-30 within 60 days and subsequently switched into neural-specifying culture medium to obtain neuronal cells in about 8-12 days (FIG. 4F). Furthermore, the XEN-like cells retained genetic integrity and genome stability after passages (FIG. 4B-C). Thus, this new lineage reprograming approach would circumvent the deep-rooted problem of limited cell yield of traditional direct reprogramming to generate sufficient number of functional cells via a highly expandable XEN-like intermediate stage.

We claim:

1. A cell culture system comprising:
a eukaryotic cell population of a first cell lineage having a cell density, wherein the cell density is as provided by a cell seeding of about 25000 to 30000 cells/well in a six well plate and suspended in a first cell culture medium composition for inducing reprogramming of eukaryotic cells in the eukaryotic cell population into eukaryotic cells of a second lineage in a second cell culture medium,
wherein the cells of the second lineage are not pluripotent,
wherein the first cell culture medium composition is effective to bias eukaryotic cells in the eukaryotic cell population into a modified extraembryonic endoderm (XEN)-like cell population which is effectively primed for reprogramming into cells of the second lineage when cultured in the second cell culture medium,
wherein the first cell culture medium comprises: TD114-2, and chemical inducers of lineage reprogramming (CiLRs) from each of the following groups:
(a) TGFβ receptor inhibitors,
(b) cyclic AMP (cAMP) agonists,
(c) histone acetylators,
(d) DOT1L methyltransferase inhibitors,
(e) a retinoic acid receptor (RAR) agonist, and
(f) inhibitors of histone demethylation,
wherein the second culture medium is a lineage specific cell medium for the cells of the second lineage.

2. The cell culture system of claim 1, wherein:
(a) the TGFβ receptor inhibitor is selected from the group consisting of 616452 (6), SB431542 (S), LDN 193189 (L), and dorsomorphin (D);
(b) the cAMP agonist is Forskolin (F);
(c) the DOT1L methyltransferase inhibitor is EPZ004777 (E);
(d) the RAR agonist is AM 580 (A);
(e) the histone acetylator is valproic acid (V); and
(f) the inhibitor of histone demethylation is tranylcypromine (T).

3. The cell culture system of claim 2, comprising:
(i) V6TFEA-TD114-2, wherein, V is in a concentration range from 100-500 µM; 6 is in a concentration range from 5-10 µM; F is in a concentration range from 5-100 µM; T is in a concentration range from 1-5 µM; F is in a concentration range from 50-100 µM; E is in a concentration range from 1-5 µM; A is in a concentration range from 0.01-0.05 µM; and TD114-2 is in a concentration range from 2-6 µM; or
(ii) FCD, further optionally comprising L and/or S.

4. The cell culture system of claim 1, wherein the composition does not include ISX9.

5. The cell culture system of claim 1, wherein the eukaryotic cell population of a first lineage is selected from the group consisting of derived cells, fibroblasts, adipose cells, epithelial cells, endothelial cells, mesenchymal cells, parenchymal cells, neurological cells, connective tissue cells, adipose-derived cells, and intestinal epithelial cells.

6. The cell culture system of claim 1, wherein the eukaryotic cell population of a first lineage comprises fibroblasts.

* * * * *

SEQUENCE LISTING

<160> NUMBER OF SEQ ID NOS: 54

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
catgttccag tatgactcca ctc                                    23

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ggcctcaccc catttgatgt                                       20

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
cgggaagcgt gtacttatcc tt                                    22

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
gcggagtgga aactttttgtc c                                    21

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
cagggctttc atgtcctgg                                        19

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
agttggcgtg gagactttgc                                       20

<210> SEQ ID NO 7
<211> LENGTH: 19
<212> TYPE: DNA
<213> ORGANISM: Artificial Sequence
<220> FEATURE:
<223> OTHER INFORMATION: Synthetic primer

<400> SEQUENCE: 7
gtggctgagg gcatcaatg                                        19

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
aaccgaatgt cgtccgaaga c                                     21

<210> SEQ ID NO 9

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
agttatggag cggagcagca t                                              21

<210> SEQ ID NO 10
<211> LENGTH: 18
<212> TYPE: DNA
<213> ORGANISM: Artificial Sequence
<220> FEATURE:
<223> OTHER INFORMATION: Synthetic primer

<400> SEQUENCE: 10
aggcctggac cgctcagt                                                  18

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tgaggtggtc gcttgtgtag                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
atggcgtaga aatgctgagg                                                20

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
gagctggcct gcgatgtctg agtg                                           24

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
aaacggaagc ccaagaacct gaat                                           24

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
```

```
gtcaacgcct tccaagactt g                                          21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
gtaaaggtga aaggcgaggt g                                          21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
acttgaactc tatggcgggt t                                          21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
ccagttggta aagtccagca g                                          21

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
gacaagatcg cagcgcaagg                                            20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ggcttagggc atttgaggaa                                            20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
acgcagaagg caaggtgtcc                                            20

<210> SEQ ID NO 22
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 22
gttcctcgtc ctgagaactg                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tggctggcat ctgctctatt                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
taggcattgt gacgaatctg                                                    20

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
catgttcagc tttgtggacc t                                                  21

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gcagctgact tcagggatgt                                                    20

<210> SEQ ID NO 27
<211> LENGTH: 24
<212> TYPE: DNA
<213> ORGANISM: Artificial Sequence
<220> FEATURE:
<223> OTHER INFORMATION: Synthetic primer

<400> SEQUENCE: 27
gtgtccacct tccacaaata ctca                                               24

<210> SEQ ID NO 28
<211> LENGTH: 23
<212> TYPE: DNA
<213> ORGANISM: Artificial Sequence
<220> FEATURE:
<223> OTHER INFORMATION: Synthetic primer

<400> SEQUENCE: 28
acttcattgt ccctgttgct gtc                                                23
```

<210> SEQ ID NO 29
<211> LENGTH: 24
<212> TYPE: DNA
<213> ORGANISM: Artificial Sequence
<220> FEATURE:
<223> OTHER INFORMATION: Synthetic primer

<400> SEQUENCE: 29
gcacttccta gatgacaagg gaca                                              24

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
caggctcaac gggacaagaa                                                   20

<210> SEQ ID NO 31
<211> LENGTH: 18
<212> TYPE: DNA
<213> ORGANISM: Artificial Sequence
<220> FEATURE:
<223> OTHER INFORMATION: Synthetic primer

<400> SEQUENCE: 31
catcaccacc atcgtcaa                                                     18

<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32
cctcgtgtca catcttctt                                                    19

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
atgttaccaa gtgctgtagt                                                   20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
aatctgcttc tccttctctg                                                   20

<210> SEQ ID NO 35
<211> LENGTH: 22
<212> TYPE: DNA
<213> ORGANISM: Artificial Sequence
<220> FEATURE:

<223> OTHER INFORMATION: Synthetic primer

<400> SEQUENCE: 35
ttcctgtctc agtcattcta ag                                           22

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
agtctcctaa ggtctggtag                                              20

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
tactgtgatg gagatggaat ac                                           22

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
ggtgaagagc ataagatgga                                              20

<210> SEQ ID NO 39
<211> LENGTH: 18
<212> TYPE: DNA
<213> ORGANISM: Artificial Sequence
<220> FEATURE:
<223> OTHER INFORMATION: Synthetic primer

<400> SEQUENCE: 39
ctcaccacag atgagaag                                                18

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
ggctgagtct ctcaattc                                                18

<210> SEQ ID NO 41
<211> LENGTH: 22
<212> TYPE: DNA
<213> ORGANISM: Artificial Sequence
<220> FEATURE:
<223> OTHER INFORMATION: Synthetic primer

<400> SEQUENCE: 41
aaataagcgt ccgtccaaag aa                                           22

```
<210> SEQ ID NO 42
<211> LENGTH: 21
<212> TYPE: DNA
<213> ORGANISM: Artificial Sequence
<220> FEATURE:
<223> OTHER INFORMATION: Synthetic primer

<400> SEQUENCE: 42
gacgatgaac tgcctgagtt g                                          21

<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
agtgctggtg aaggaatg                                              18

<210> SEQ ID NO 44
<211> LENGTH: 18
<212> TYPE: DNA
<213> ORGANISM: Artificial Sequence
<220> FEATURE:
<223> OTHER INFORMATION: Synthetic primer

<400> SEQUENCE: 44
ctggtgaagg ttggagac                                              18

<210> SEQ ID NO 45
<211> LENGTH: 19
<212> TYPE: DNA
<213> ORGANISM: Artificial Sequence
<220> FEATURE:
<223> OTHER INFORMATION: Synthetic primer

<400> SEQUENCE: 45
gtccatcctc cagaacttc                                             19

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
ttccaatacc actctccttg                                            20

<210> SEQ ID NO 47
<211> LENGTH: 21
<212> TYPE: DNA
<213> ORGANISM: Artificial Sequence
<220> FEATURE:
<223> OTHER INFORMATION: Synthetic primer

<400> SEQUENCE: 47
cgtgaatcgg cactctacag c                                          21

<210> SEQ ID NO 48
<211> LENGTH: 23
<212> TYPE: DNA
<213> ORGANISM: Artificial Sequence
<220> FEATURE:
<223> OTHER INFORMATION: Synthetic primer
```

```
<400> SEQUENCE: 48
tgcaccttgt gtctctttac ctc                                          23

<210> SEQ ID NO 49
<211> LENGTH: 21
<212> TYPE: DNA
<213> ORGANISM: Artificial Sequence
<220> FEATURE:
<223> OTHER INFORMATION: Synthetic primer

<400> SEQUENCE: 49
aacatggagc ccttgcgtaa a                                            21

<210> SEQ ID NO 50
<211> LENGTH: 21
<212> TYPE: DNA
<213> ORGANISM: Artificial Sequence
<220> FEATURE:
<223> OTHER INFORMATION: Synthetic primer

<400> SEQUENCE: 50
atgagcacat catcaggcca g                                            21

<210> SEQ ID NO 51
<211> LENGTH: 19
<212> TYPE: DNA
<213> ORGANISM: Artificial Sequence
<220> FEATURE:
<223> OTHER INFORMATION: Synthetic primer

<400> SEQUENCE: 51
aggctcgtgc tcgtgtaga                                               19

<210> SEQ ID NO 52
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
cagggaacat caccttatgc c                                            21

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
cgccaccagt tcgccatgga                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic primer

<400> SEQUENCE: 54
tacagcccgg ggagcatcgt                                              20
```